United States Patent
Kong et al.

(10) Patent No.: US 9,752,177 B2
(45) Date of Patent: Sep. 5, 2017

(54) FILTERING SMALL NUCLEIC ACIDS USING PERMEABILIZED CELLS

(71) Applicant: Bio-Rad Laboratories, Inc., Hercules, CA (US)

(72) Inventors: Yanhong Kong, Hercules, CA (US); Steven T. Okino, San Carlos, CA (US); Xiangdong Meng, Albany, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 292 days.

(21) Appl. No.: 14/256,861

(22) Filed: Apr. 18, 2014

(65) Prior Publication Data

US 2014/0220586 A1 Aug. 7, 2014
US 2016/0208312 A9 Jul. 21, 2016

Related U.S. Application Data

(63) Continuation of application No. 13/565,464, filed on Aug. 2, 2012, now Pat. No. 8,728,987.

(60) Provisional application No. 61/514,711, filed on Aug. 3, 2011, provisional application No. 61/570,581, filed on Dec. 14, 2011.

(51) Int. Cl.
*C12Q 1/68* (2006.01)

(52) U.S. Cl.
CPC .................. *C12Q 1/6806* (2013.01)

(58) Field of Classification Search
None
See application file for complete search history.

(56) References Cited

U.S. PATENT DOCUMENTS

| | | |
|---|---|---|
| 5,128,247 A | 7/1992 | Koller |
| 5,972,608 A | 10/1999 | Peterson et al. |
| 6,331,393 B1 | 12/2001 | Laird et al. |
| 6,492,168 B1 | 12/2002 | Kladde et al. |
| 8,652,821 B2 | 2/2014 | Okino et al. |
| 8,728,987 B2 | 5/2014 | Kong et al. |
| 9,273,347 B2 | 3/2016 | Okino |
| 2002/0177139 A1 | 11/2002 | Greenfield et al. |
| 2004/0014086 A1 | 1/2004 | Stamatoyannapoulos et al. |
| 2004/0023206 A1 | 2/2004 | Polansky |
| 2005/0079516 A1* | 4/2005 | Maniotis ............... C12Q 1/68 435/6.12 |
| 2006/0166206 A1 | 7/2006 | Urnov et al. |
| 2007/0009937 A1 | 1/2007 | Laemmli et al. |
| 2009/0130237 A1 | 5/2009 | Cohen |
| 2009/0155791 A1 | 6/2009 | Wojdacz et al. |
| 2009/0215066 A1 | 8/2009 | Ahmed et al. |
| 2009/0286304 A1 | 11/2009 | Latham et al. |
| 2010/0136559 A1 | 6/2010 | Okino et al. |
| 2011/0306042 A1 | 12/2011 | Jouvenot |
| 2012/0064517 A1 | 3/2012 | Okino et al. |
| 2012/0070829 A1 | 3/2012 | Okino et al. |
| 2012/0082991 A1 | 4/2012 | Okino |
| 2012/0100597 A1 | 4/2012 | Okino et al. |
| 2012/0208193 A1 | 8/2012 | Okino et al. |
| 2012/0322058 A1 | 12/2012 | Regan et al. |
| 2013/0035239 A1 | 2/2013 | Kong et al. |
| 2013/0109737 A1 | 5/2013 | Young et al. |
| 2016/0186258 A1 | 6/2016 | Okino |
| 2016/0273027 A1 | 9/2016 | Okino et al. |
| 2017/0159132 A1 | 6/2017 | Okino et al. |

FOREIGN PATENT DOCUMENTS

| | | |
|---|---|---|
| EP | 2 614 160 B1 | 4/2016 |
| EP | 2 675 913 B1 | 12/2016 |
| JP | 2002-209588 A | 7/2002 |
| WO | WO 00/29618 | 5/2000 |
| WO | WO 02/097135 A1 | 12/2002 |
| WO | WO 03/004702 A2 | 1/2003 |
| WO | 03/035894 A2 | 5/2003 |
| WO | WO 03/076949 | 9/2003 |
| WO | 2006/096727 A | 9/2006 |
| WO | WO 2009/061840 | 5/2009 |
| WO | WO 2010/065266 | 6/2010 |
| WO | 2012/034041 A2 | 3/2012 |
| WO | WO 2012/034007 | 3/2012 |
| WO | WO 2012/034013 | 3/2012 |
| WO | WO 2012/054613 | 4/2012 |
| WO | WO 2012/112606 | 8/2012 |
| WO | WO 2013/019960 | 2/2013 |
| WO | WO 2015/080966 | 6/2015 |

OTHER PUBLICATIONS

U.S. Appl. No. 15/034,548, filed May 5, 2016, Okino et al.
U.S. Appl. No. 15/043,552, filed Feb. 13, 2016, Okino.
US Office Action dated May 31, 2013 issued in U.S. Appl. No. 13/396,496.
US Final Office Action dated Dec. 5, 2013 issued in U.S. Appl. No. 13/396,496.
US Office Action dated Sep. 26, 2014 issued in U.S. Appl. No. 13/396,496.
US Final Office Action dated May 18, 2015 issued in U.S. Appl. No. 13/396,496.
US Office Action dated Jan. 15, 2016 issued in U.S. Appl. No. 13/396,496.
US Office Action dated Feb. 13, 2015 issued in U.S. Appl. No. 13/229,111.
US Notice of Allowance dated Aug. 4, 2015 issued in U.S. Appl. No. 13/229,111.
US Notice of Allowance dated Oct. 29, 2015 issued in U.S. Appl. No. 13/229,111.
US Restriction Requirement dated Jan. 24, 2013 issued in U.S. Appl. No. 13/276,553.
US Office Action dated Apr. 8, 2013 issued in U.S. Appl. No. 13/276,553.
US Notice of Allowance dated Oct. 8, 2013 issued in U.S. Appl. No. 13/276,553.
US Office Action dated Apr. 19, 2012 issued in U.S. Appl. No. 13/229,132.
US Final Office Action dated Sep. 20, 2012 issued in U.S. Appl. No. 13/229,132.
US Office Action dated Aug. 29, 2013 issued in U.S. Appl. No. 13/229,132.
US Final Office Action dated Feb. 5, 2014 issued in U.S. Appl. No. 13/229,132.

(Continued)

*Primary Examiner* — Karen S Weiler
(74) *Attorney, Agent, or Firm* — Weaver Austin Villeneuve & Sampson LLP

(57) ABSTRACT

Filtering small nucleic acids using permeabilized cells and methods for using the filtering to detect genomic DNA accessibility are described.

16 Claims, 15 Drawing Sheets

(56) References Cited

OTHER PUBLICATIONS

US Office Action dated Sep. 26, 2014 issued in U.S. Appl. No. 13/229,132.
US Final Office Action dated Feb. 10, 2015 issued in U.S. Appl. No. 13/229,132.
US Office Action dated Jul. 1, 2015 issued in U.S. Appl. No. 13/229,132.
US Final Office Action dated Nov. 30, 2015 issued in U.S. Appl. No. 13/229,132.
US Office Action dated May 24, 2013 issued in U.S. Appl. No. 13/565,464.
US Final Office Action dated Jan. 9, 2014 issued in U.S. Appl. No. 13/565,464.
US Notice of Allowance dated Mar. 17, 2014 issued in U.S. Appl. No. 13/565,464.
PCT International Search Report and Written Opinion, dated May 2, 2012, issued in PCT/US2012/025120.
PCT International Preliminary Report on Patentability, dated Aug. 29, 2013, issued in PCT/US2012/025120.
PCT International Search Report, dated Mar. 26, 2012, issued in PCT/US2011/050992.
PCT International Preliminary Report on Patentability, dated Mar. 21, 2013, issued in PCT/US2011/050992.
PCT International Search Report and Written Opinion, dated Feb. 22, 2012, issued in PCT/US2011/056900.
PCT International Preliminary Report on Patentability, dated May 2, 2013, issued in PCT/US2011/056900.
PCT International Search Report, dated Mar. 26, 2012, issued in PCT/US2011/050981.
PCT International Preliminary Report on Patentability and Written Opinion, dated Mar. 21, 2013, issued in PCT/US2011/050981.
PCT International Search Report, dated Oct. 22, 2012, issued in PCT/US2012/049344.
PCT International Preliminary Report on Patentability and Written Opinion, dated Feb. 13, 2014, issued in PCT/US2012/049344.
PCT International Search Report and Written Opinion, dated Feb. 25, 2015, issued in PCT/US2014/066822.
PCT International Preliminary Report on Patentability, dated Jun. 9, 2016, issued in PCT/US2014/066822.
Chinese First Office Action, dated Dec. 8, 2014, issued in CN 201280038451.3.
Chinese Second Office Action, dated Jun. 24, 2015, issued in CN 201280038451.3.
Chinese Decision of Rejection, dated Feb. 2, 2016, issued in CN 201280038451.3.
European Search Report, dated Dec. 17, 2014, issued in EP Application No. 12 705 595.2.
European Office Action dated Feb. 2, 2016 issued in EP Application No. 12 705 595.2.
European Extended European Search Report dated Dec. 20, 2013 issued in EP Application No. 11 824 173.6.
European Office Action dated Sep. 11, 2014 issued in EP Application No. 11 824 173.6.
European Extended Search Report dated Feb. 20, 2014 issued in EP 11 824 170.2.
European Office Action dated Feb. 12, 2016 issued in EP 11 824 170.2.
European Office Action dated Apr. 7, 2016 issued in EP Application No. 12 819 299.4.
Japanese Office Action (Notice of Reasons for Rejection) dated Sep. 7, 2015 issued in JP 2013-528327.
Japanese Office Action dated Jul. 6, 2015 issued in JP 2013-528325.
Almeida, (Jan. 6, 2009) "Polymorphisms and DNA methylation of gene TP53 associated with extraaxial brain tumors," *Genet Mol Res.*, 8(1):8-18 (abstract only), 2 pages.
Antequera et al., (Aug. 10, 1990) "High levels of de novo methylation and altered chromatin structure at CpG islands in cell lines," *Cell*. 62(3):503-14.
Arnold et al., (1996) "Thermal unfolding and proteolytic susceptibility of ribonuclease A," *Eur. J. Biochem.*, 237:862-869.

ARUP Laboratories, (Jan. 2012) "Septin 9 (*SEPT9*) Methylated DNA Detection by Real-Time PCR," *National Reference Laboratory*, 2 pages.
Barski, (May 2010) "Hypermethylation and transcriptional downregulation of the TIMP3 gene is associated with allelic loss on 22q12.3 and malignancy in meningiomas," *Brain Pathol.*20(3):623-31 (abstract only), 2 pages.
Barton, (Jan. 5, 2010) "Collagen and calcium-binding EGF domains 1 is frequently inactivated in ovarian cancer by aberrant promoter hypermethylation and modulates cell migration and survival," *Br J Cancer*.102(1):87-96 (abstract only), 2 pages.
Bennett, (Apr. 2010) "HPV status-independent association of alcohol and tobacco exposure or prior radiation therapy with promoter methylation of FUSSEL18, EBF3, IRX1, and SEPT9, but not SLC5A8, in head and neck squamous cell carcinomas," *Genes Chromosomes Cancer*,49(4):319-26 (abstract only), 2 pages.
Berdasco, (Dec. 22, 2009) "Epigenetic inactivation of the Sotos overgrowth syndrome gene histone methyltransferase NSD1 in human neuroblastoma and glioma," *Proc Natl Acad Sci USA* 106(51):21830-5 (abstract only), 2 pages.
Bryan, (Nov. 13, 2009) "Hypermethylation of the DLC1 CpG island does not alter gene expression in canine lymphoma," *BMC Genet.*,10:73 (abstract only), 2 pages.
Buryanov et al., (2005) "The use of prokaryotic DNA methyltransferases as experimental and analytical tools in modern biology," *Analytical Biochemistry*, Academic Press Inc., New York, 338:1-11.
Carthew et al., (Feb. 20, 2009) "Origins and Mechanisms of miRNAs and siRNAs," *Cell*, 136(4):642-655.
Chen et al., (Nov. 2001) "Nucleosomes Are Translationally Positioned on the Active Allele and Rotationally Positioned on the Inactive Allele of the *HPRT* Promoter," *Molecular and Cellular Biology*, 21(22):7682-7695.
Chen, (Oct. 22, 2009) "Loss of prostasin (PRSS8) in human bladder transitional cell carcinoma cell lines is associated with epithelial-mesenchymal transition (EMT)," *BMC Cancer*, 9:377 (abstract only), 2 pages.
Cheng, (Feb. 2010) "Reduced CRYL1 expression in hepatocellular carcinoma confers cell growth advantages and correlates with adverse patient prognosis," *J Pathol.*,220(3):348-60 (abstract only), 2 pages.
Chim, (Dec. 2008) "Gene hypermethylation in multiple myeloma: lessons from a cancer pathway approach," *Clin Lymphoma Myeloma.*, 8(6):331-9 (abstract only), 2 pages.
Crawford et al., (Jan. 27, 2004) "Identifying gene regulatory elements by genome-wide recovery of DNase hypersensitive sites," *Proc Natl Acad Sci USA*, 101(4):992-997.
Crawford et al., (Jul. 2006) "Dnase-chip: a high-resolution method to identify Dnase I hypersensitive sites using tiled microarrays," *Nat Methods.*, 3(7):503-509.
Crawford et al., (2006) "Genome-wide mapping of Dnase hypersensitive sites using massively parallel signature sequencing (MPSS)," *Genome Research*, 16:123-131.
Dingwall et al., (1981) "High sequence specificity of micrococcal nuclease," *Nucleic Acids Research* 9(12):2659-2673.
Epigenomics 2009 "The Septin 9 test—A simple blood-based test for early detection of colorectal cancer," p. 1-4.
Eurofins. LightCycler Probes for FRET Assays [online] Aug. 29, 2013 [retrieved Jan. 28, 2015]. Available on the internet:<https://web.archive.org/web/20130829020418/http://www.eurofinsgenomics.eu/en/dna-ma-oligonucleotides/optimised-application-oligos/qpcr-probes/lightcycler-probes.aspx>, 1 page.
Fackler et al., (2003) "DNA Methylation of *RASSF1A, HIN-1, RAR-β, Cyclin D2* and *Twist* in in Situ and Invasive Lobular Breast Carcinoma," *Int. J. Cancer*: 107:970-975.
Fackler, (Jun. 1, 2009) "Hypermethylated genes as biomarkers of cancer in women with pathologic nipple discharge," *Clin Cancer Res.*, 15(11):3802-11 (abstract only), 2 pages.
Ferrai et al., (Apr. 27, 2007) A Transcription-dependent Micrococcal Nuclease-resistant Fragment of the Urokinase-type Plasminogen Activator Promoter Interacts with the Enhancer, *The Journal of Biological Chemistry*, 282(17):12537-12546.

(56) References Cited

OTHER PUBLICATIONS

Foltz, (Jul. 23, 2009) "DNA methyltransferase-mediated transcriptional silencing in malignant glioma: a combined whole-genome microarray and promoter array analysis," *Oncogene*,28(29):2667-77 (abstract only), 2 pages.
Fu, (Nov. 2009) "Hypermethylation of APC promoter 1A is associated with moderate activation of Wnt signalling pathway in a subset of colorectal serrated adenomas," *Histopathology*,55(5):554-63 (abstract only), 2 pages.
Genomic imprinting from Wikipedia, the free encyclopedia. Printed on May 24, 2013, [Retrieved at http://en.wikipedia.org/wiki/Genomic imprinting on May 24, 2013], 10 pages.
Götze et al., (Dec. 17, 2009) "ECRG4 is a candidate tumor suppressor gene frequently hypermethylated in colorectal carcinoma and glioma," *BMC Cancer*, 9:447 (abstract only), 2 pages.
Grau et al., (Mar. 2011) "Hypermethylation of apoptotic genes as independent prognostic factor in neuroblastoma disease," *Mol Carcinog.*, 50(3):153-62 (abstract only), 2 pages.
Hagège et al. (2007) "Quantitative analysis of chromosome conformation capture assays (3C-qPCR)," *Nature Protocols* 2(7):1722-1733.
Hamilton et al., (Dec. 15, 2009) "ATM regulates a RASSF1A-dependent DNA damage response," *Curr Biol.* 19(23):2020-5 (abstract only), 2 pages.
Huang et al., (Jan. 2010) "Genetic and epigenetic silencing of SCARA5 may contribute to human hepatocellular carcinoma by activating FAK signaling," *J Clin Invest.*, 120(1):223-41 (abstract only), 2 pages.
Ignatov et al. (Feb. 2010) "APC promoter hypermethylation is an early event in endometrial tumorigenesis," *Cancer Sci.*, 101(2):321-7 (abstract only), 2 pages.
Indovina et al. (Apr. 2010) "Downregulation and aberrant promoter methylation of p16INK4A: a possible novel heritable susceptibility marker to retinoblastoma," *J Cell Physiol.*, 223(1): 143-50 (abstract only), 2 pages.
Isomoto, (2009) "Epigenetic alterations in cholangiocarcinoma-sustained IL-6/STA T3 signaling in cholangio-carcinoma due to SOCS3 epigenetic silencing," *Digestion*, 79:Suppl 1:2-8 (abstract only), 2 pages.
Jha et al., (2010) "Reversal of hypermethylation and reactivation of the RAR~2 gene by natural compounds in cervical cancer cell lines," *Folia Biol* (Praha), 56(5):195-200 (abstract only), 1 page.
Jones et al., (Jun. 2002) "The fundamental role of epigenetic events in cancer," *Nat Rev Genet.* 3(6):415-28.
Kanduri, (Jan. 14, 2010) "Differential genome-wide array-based methylation profiles in prognostic subsets of chronic lymphocytic leukemia," *Blood*,115(2):296-305 (abstract only), 2 pages.
Kauffmann et al., (2009) "Improvement of RNA secondary structure prediction using RNase H cleavage and randomized oligonucleotides," *Nucleic Acids Res.*, 37(18):e121, 11 pages.
Kim et al., (Dec. 2009) "Borderline and malignant phyllodes tumors display similar promoter methylation profiles," *Virchows Arch.*, 455(6):469-75 (abstract only), 2 pages.
Kron et al., (2009) "Discovery of novel hypermethylated genes in prostate cancer using genomic CpG island microarrays," *PLoS One*,4(3):e4830 (abstract only), 2 pages.
Kulis et al., (2010) "DNA methylation and cancer," *Advances in Genetics*, 70, 27-56 (Abstract only, 2 pages).
Kuo, M. Tien, (1979) "Studies in Heterochromatin DNA: Accessibility of Late Replicating Heterochromatin DNA in Chromatin to Micrococcal Nuclease Digestion," *Chromosoma* (Berl.) 70:183-194.
Kwabi-Addo et al., (2007) "Age-related DNA methylation changes in normal human prostate tissues," *Clin. Cancer Res.*, 13:3796-3802.
Laurent-Puig et al., (Nov. 2010) "Colorectal oncogenesis," *Bull Cancer*, 97(11):1311-21 (abstract only), 2 pages.
Lewis, Matt "Agarose gel electrophoresis (basic method)," Loading Buffer Recipe from Matt Lewis—Methodbook.net [retrieved on Mar. 28, 2013 at http://www.methodbook.net/dna/agarogel.html#loadingbuff ] copyright 2001, 5 pages.
Liu et al., (Jul. 2009) "Methylation status of RASSF1A and DAPK promoter in retinoblastoma," *Zhonghua YanKe Za Zhi.*, 45(7):631-5 (abstract only), 2 pages.
Liu et al., (May 27, 2009) "The 14-3-3sigma gene promoter is methylated in both human melanocytes and melanoma," *BMC Cancer*, 9:162 (abstract only), 2 pages.
Lyn-Cook et al., (Dec. 2010) "Gender differences in gemcitabine (Gemzar) efficacy in cancer cells: effect ofindole-3-carbinol," *Anticancer Res.*30(12):4907-13 (abstract only), 1 page.
Ma et al., (2010) "The relationship between methylation of the Syk gene in the promoter region and the genesis of lung cancer," *Clin Lab.*, 56(9-10):407-16 (abstract only), 2 pages.
Majid et al., (Jan. 1, 2010) "Genistein reverses hypermethylation and induces active histone modifications in tumor suppressor gene B-Cell translocation gene 3 in prostate cancer," *Cancer*,116(1):66-76 (abstract only), 2 pages.
Martin et al., (Feb. 2010) "Epigenetic regulation of the non-canonical Wnt pathway in acute myeloid leukemia," *Cancer Sci.* 101(2):425-32 (abstract only), 2 pages.
Martinez et al., (May 16, 2009) "A microarray-based DNA methylation study of glioblastoma multiforme," *Epigenetics*, 4(4):255-64 (abstract only), 2 pages.
Masson et al. (Jul. 10, 1996) "Conditions favoring RNA polymerase 1 transcription in permeabilized cells," *Exp Cell Res*, 226(1):114-125.
Meijer et al., (1996) "Use of Mitochondrial DNA as a Sensitive and Specific Marker for Localization of Mitochondria in Fractionated Plant Extracts," *Plant Molecular Biology Reporter*, 14(4):353-362.
Melotte et al., (Jul. 1, 2009) "N-Myc downstream-regulated gene 4 (NDRG4): a candidate tumor suppressor gene and potential biomarker for colorectal cancer," *J Natl Cancer Inst.*, 101(13):916-27 (abstract only), 2 pages.
Micard et al., (Jul. 1985) "Purification of RNA-free plasmid DNA using alkaline extraction followed by Ultrogel A2 column chromatography," *Anal Biochem.*, 148(1):121-126, Abstract, 2 pages.
Moncada-Pazos et al., (Aug. 15, 2009) "The ADAMTS12 metalloprotease gene is epigenetically silenced in tumor cells and transcriptionally activated in the stroma during progression of colon cancer," *J Cell Sci.* 122(Pt 16):2906-13 (abstract only), 2 pages.
Morris et al., (Mar. 24, 2011) "Genome-wide methylation analysis identifies epigenetically inactivated candidate tumour suppressor genes in renal cell carcinoma," *Oncogene*,30(12):1390-401 (abstract only), 2 pages.
Niklinska et al., (2009) "Prognostic significance of DAPK and RASSF1A promoter hypermethylation in non-small cell lung cancer (NSCLC)," *Folia Histochem Cytobiol.* 47(2):275-80 (abstract only), 2 pages.
Nomoto et al., (Mar. 2010) "Epidermal growth factor-containing fibulin-like extracellular matrix protein 1, EFEMP1, a novel tumor-suppressor gene detected in hepatocellular carcinoma using double combination array analysis," *Ann Surg Oneal.*,17(3):923-32 (abstract only), 2 pages.
Nuovo et al., (Oct. 26, 1999) "In situ detection of the hypermethylation-induced inactivation of the *p16* gene as an early event in oncogenesis," *Proc Natl Acad Sci USA*, 6(22):12754-9.
Ogawa et al., (Jun. 6, 2008) "Intersection of the RNA Interference and X-Inactivation Pathways," *Science*, 320:1336-1341.
Paluszczak et al., (Feb. 2011) "Frequent gene hypermethylation in laryngeal cancer cell lines and the resistance to demethylation induction by plant polyphenols," *Toxicol In Vitro.* 25(1):213-21 (abstract only), 2 pages.
Park et al., (Jan. 2011) "Promoter CpG island hypermethylation during breast cancer progression," *Virchows Arch.*, 458(1):73-84 (abstract only), 2 pages.
Poetsch et al. (Feb. 2011) "Alterations in the tumor suppressor gene p16(INK4A) are associated with aggressive behavior of penile carcinomas," *Virchows Arch.* 458(2):221-9 (abstract only), 2 pages.
"Properties of Exonucleases and Endonucleases," *New England Biolabs, Inc.* [Retrieved at https://www.neb.com/tools-andresources/selection-charts/properties-of-exonucleases-and-endonucleases on Jul. 17, 2015], 2 pages.

(56) References Cited

OTHER PUBLICATIONS

Pulling et al., (Dec. 2009) "Dual promoter regulation of death-associated protein kinase gene leads to differentially silenced transcripts by methylation in cancer," *Carcinogenesis*, 30(12):2023-30 (abstract only), 2 pages.
Qian et al., (Jun. 2011) "Abnormal methylation of GRAF promoter Chinese patients with acute myeloid leukemia," *Leuk Res.*, 35(6):783-6 (abstract only), 2 pages.
Rivero-Muller et al., (Feb. 13, 2007) "Mixed chelate copper complex, Casiopeina IIgly®, binds and degrades nucleic acids: A mechanism of cytotoxicity," *Chemico-Biological Interactions*, Elsevier Science, Ireland, 165(3):189-199.
Rodriguez-Campos et al., (Nov. 2007) "RNA is an integral component of chromatin that contributes to its structural organization," *PLOS One* 2(11):e1182, 12 pages.
Röhrs et al., (Oct. 16, 2009) "Hypomethylation and expression of BEX2, IGSF4 and TIMP3 indicative of MLL translocations in acute myeloid leukemia," *Mol Cancer*, 8:86 (abstract only), 2 pages.
Sakamoto et al., (Apr. 2010) "MT1G hypermethylation: a potential prognostic marker for hepatoblastoma," *Pediatr Res.*,67(4):387-93 (abstract only), 2 pages.
Sambrook et al., (2001) "Protocol 1—Mapping Protein-binding Sites on DNA by DNase 1 Footprinting," and "Protocol 3—Mapping DNase-1-hypersensitive Sites," *Molecular Cloning: A Laboratory manual*, 3rd edition Cold Spring Harbor Laboratory Press, New York, Chapter 17, pp. 17.4-17.12 and 17.18-17.22, 14pp.
Sasahira et al., (Feb. 2011) "Downregulation of runt-related transcription factor 3 associated with poor prognosis of adenoid cystic and mucoepidermoid carcinomas of the salivary gland," *Cancer Sci.*, 102(2):492-7 (abstract only), 2 pages.
Schagdarsurengin et al., (Nov. 16, 2009) "Frequent epigenetic inactivation of RASSF10 in thyroid cancer," *Epigenetics*,4(8):571-6 (abstract only), 1 page.
Sharma et al., (2009) "Prognostic relevance of promoter hypermethylation of multiple genes in breast cancer patients," *Cell Oncol.*,31(6):487-500 (abstract only), 2 pages.
Steinmann et al., (Dec. 2009) "Frequent promoter hypermethylation of tumor-related genes in head and neck squamous cell carcinoma," *Oncol Rep.*22(6):1519-26 (abstract only), 2 pages.
Stephen et al., (Jan. 2009) "DNA hypermethylation profiles in squamous cell carcinoma of the vulva," *Int J Gynecol Pathol.*, 28(1):63-75 (abstract only), 2 pages.
Syeed et al., (Feb. 10, 2011) "Mutational and promoter hypermethylation status of FHIT gene in breast cancer patients of Kashmir," *Mutat Res.*, 707(1-2):1-8 (abstract only), 2 pages.
Tan et al. (2010) "Manipulation and Isolation of Single Cells and Nuclei," *Methods Cell Biol*, 98:79-96.
Tänzer et al., (Feb. 4, 2010) "Performance of epigenetic markers SEPT9 and ALX4 in plasma for detection of colorectal precancerous lesions," *PLoS One*, 5(2):e9061, 6 pages.
Tokuyama, (Dec. 2010) "Aberrant Methylation of Heparan Sulfate Glucosamine 3-*O*-Sulfotransferase 2 Genes as a Biomarker in Colorectal Cancer," *Anticancer Res*. 30(12):4811-4818.
Tomita et al., (Mar. 2011) "Inhibition of gastric carcinogenesis by the hormone gastrin is mediated by suppression of TFF1 epigenetic silencing," *Gastroenterology*, 140(3):879-91 (abstract only), 2 pages.
Toyota et al., (1999) "CpG island methylator phenotypes in aging and cancer," *Seminars in Cancer Biology*, 9:349-357.
Tung et al., (Apr. 15, 2009) "HAI-2 is epigenetically downregulated in human hepatocellular carcinoma, and its Kunitz domain type 1 is critical for anti-invasive functions," *Int J Cancer.*, 124(8):1811-9 (abstract only), 2 pages.
Wang et al., (Oct. 19, 2009) "CHD5 is down-regulated through promoter hypermethylation in gastric cancer," *J Biomed Sci*. 16:95 (abstract only), 2 pages.
Wu et al., (Jun. 1, 2010) "Glutamate receptor, ionotropic, kainate 2 silencing by DNA hypermethylation possesses tumor suppressor function in gastric cancer," *Int J Cancer*,126(11):2542-52 (abstract only), 2 pages.

Xu, et al., (Feb. 2011) "BCL2L10 protein regulates apoptosis/proliferation through differential pathways in gastric cancer cells," *J Pathol*. 223(3):400-9 (abstract only), 2 pages.
Yao et al., (Jul. 2011) "Aberrant methylation of CCAAT/enhancer binding protein zeta promoter in acute myeloid leukemia," *Leuk Res.*, 35(7):957-60 (abstract only), 2 pages.
Yu et al., (May 28, 2009) "TSC-22 contributes to hematopoietic precursor cell proliferation and repopulation and is epigenetically silenced in large granular lymphocyte leukemia," *Blood*, 113(22):5558-67 (abstract only), 2 pages.
Zare et al., (Jan. 17, 2009) "Qualitative analysis of Adenomatous Polyposis Coli promoter: hypermethylation, engagement and effects on survival of patients with esophageal cancer in a high risk region of the world, a potential molecular marker," *BMC Cancer*, 9:24 (abstract only), 2 pages.
Zaret K., (2005) "Micrococcal Nuclease Analysis of Chromatin Structure," *Current Protocols in Molecular Biology*, Supplement 69:21.1.1-21.1.17.
Zhang et al., (Nov. 2011) "The neuronal pentraxin II gene (NPTX2) inhibit proliferation and invasion of pancreatic cancer cells in vitro," *Mol Biol Rep.*, 38(8):4903-11 (abstract only), 2 pages.
Supplementary European Search Report from EP Application No. 12819299.4, dated Feb. 5, 2015.
The International Search Report from PCT/US2012/043944, dated Oct. 22, 2012 (3 pages).
Boyle, Alan P. et al., "High-resolution mapping and characterization of open chromatin across the genome," Cell, Jan. 25, 2008, vol. 132, pp. 311-322.
Clarke et al., "Continuous base identification for single-molecule nanopore DNA sequencing," Nature Nanotechnology, 2009, vol. 4, pp. 265-270.
Darzynkiewicz et al.; "Features of apoptotic cells measured by flow cytometry"; Cytometry; 13(8):795-808 (Jun. 1992).
Djeliova, Vera et al., "DNase 1 sensitive site in the core region of the human beta-globin origin of replication," *Journal of Cellular Biochemistry, Wiley-Liss*, US, vol. 87, No. 3, pp. 279-283 (Jan. 1, 2002).
Drouin et al., "Chaptre de livre: In vivo DNA analysis," Jan. 2001, Methods Mol Biol,; 148: 175-219.
Eberhart, Derek E. et al.; "Nuclease Sensitivity of Permeabilized Cells Confirms Altered Chromatin Formation at the Fragile X Locus"; 1996, Somatic Cell and Molecular Genetics, vol. 22, No. 6, pp. 435-441.
Eid et al, "Real-time DNA sequencing from single polymerase molecules," Science, 2009, vol. 323, pp. 133-138.
Fatemi et al., "Footprinting of mammalian promoters: use of a CpG DNA methyltransferase revealing mucleosome positions at a single molecule level", Nucleic Acids Research, 2005, 33(20):e176, pp. 1-9.
Flusberg et al., "Direct detection of DNA methylation during single-molecule, real-time sequencing," Nature Methods, 2010, vol. 7, pp. 461-465.
Guldberg, P. et al.; "Profiling DNA methylation by melting analysis"; 2002, Methods, vol. 27, No. 2, pp. 121, abstract.
Hajkova, Petra et al., "DNA-methylation analysis by the bisulfite-assisted genomic sequencing method," Methods in Molecular Biology, 2002, DNA Methylation Protocols, vol. 200, pp. 143-154.
Hernandez-Munain, C. et al. Cooperation among multiple transcription factors is required for access to minimal T-cell receptor alpha-enhancer chromatin in vivo. Mol. and Cell. Biology, vol. 18, No. 6, pp. 3223-3233, 1998.
Hughes et al., "Widespread aneuploidy revealed by DNA microarray expression profiling," Nature, 2000, vol. 25, pp. 333-337.
Jacinto et al., "Methyl-DNA immunoprecipitation (MeDIP): Hunting down the DNA methylome," Biotechniques, Jan. 2008;44(1):35, 37, 39 passim.
Jessen et al., "Mapping chromatin structure in vivo Using DNA methyltransferase," Methods, 2004, vol. 33, pp. 68-80.
Kang, SHS et al. Role of the promoter in maintaining transcriptionally active chromatin structure and DNA methylation patterns in vivo. Mol. and Cell. Biology, vol. 23, No. 12, pp. 4150-4161, 2003.
Katsnelson, "Genomics goes beyond DNA sequence," Nature, 2010, vol. 465:145.

(56) References Cited

OTHER PUBLICATIONS

Kitzis et al., "Localization of phosphoproteins and of protein kinases in chromatin from hepatoma tissue-cultured cells," Eur J Biochem, 1980, vol. 11, No. 1, pp. 237-244.
Kladde, Michael P. et al.; "Positioned nucleosomes inhibit Dam methylation in vivo"; 1994, Proceedings of the National Academy of Science, vol. 91, pp. 1361-1365.
Ko et al. "Dioxin-induced CYP1A1 transcription in vivo: the aromatic hydrocarbon receptor mediates transactivation, enhancer-promoter communication, and changes in chromatin structure," 1996, Molecular and Cellular Biology, vol. 16, No. 1, pp. 430-436.
Ko et al., "Transactivation domains facilitate promoter occupancy for the dioxin-inducible CYP1A1 gene in vivo," 1997, Molecular and Cellular Biology, vol. 17, No. 7, pp. 3497-3507.
Lee et al., "PLP2/A4 interacts with CCR1 and stimulates migration of CCR1-expressing HOS cells," Biochemical and Biophysical Research Communications, 2004, vol. 324, pp. 768-772.
Matarazzo et al., "In vivo analysis of DNA methylation patterns recognized by specific proteins: coupling ChIP and bisulfite analysis," Biotechniques, Oct. 2004;37(4):666-8, 670, 672-3.
Mellott et al., "Cytokine-induced changes in chromatin structure and in vivo footprints in the inducible NOS promoter," 2001, Am. J. Physiol. Lung Cell Mol. Physiol., 280, L390-L399.
MUGgERUD et al, "Frequent aberrant DNA methylation of *ABCB1, FOXC1, PPP2R2B* and *PTEN* in ductal carcinoma in situ and early invasive breast cancer," Breast Cancer Research, 2010;12:R3.
Narita et al.; "Rb-mediated heterochromatin formation and silencing of E2F target genes during cellular senescence"; Cell; 113(6):703-716 (Jun. 2003).
Okino et al., "Chromatin changes on the GSTP1 promoter associated with its inactivation in prostate cancer," 2007, Molecular Carcinogenesis, vol. 46, No. 10, 839-846.
Okino et al., "Dioxin induces localized, graded changes in chromatin structure: implications for Cyp1A1 gene transcription," 1995, Molecular and Cellular Biology, vol. 15, No. 7, 3714-3721.
Okino et al., Hypoxia-inducible Mammalian Gene Expression Analyzed in Vivo at a TATA-driven Promoter and at an Initiator-driven Promoter, 1998, Journal of Biological Chemistry, vol. 273, No. 37, pp. 23837-23843.
Ozsolak et al., "High-throughput mapping of the chromatin structure of human promoters," Nature Biotechnology, Feb. 2007, vol. 25, No. 2, pp. 244-248.
Patel et al., "Aberrant silencing of the CpG island-containing human O6-methylguanine DNA methyltransferase gene is associated with the loss of nucleosome-like positioning," 1997, Molecular and Cellular Biology, vol. 17, No. 10, pp. 5813-5822.
Pfeifer et al.; "Chromatin differences between active and inactive X chromosomes revealed by genomic footprinting of permeabilized cells using DNase I and ligation-mediated PCR"; Genes Dev.; 5(6):1102-1113 (Jun. 1991).
QIAquick® Spin Handbook, sold by Qiagen, published Mar. 2008, 44 pages.
Rao et al., "Chromatin Remodeling, Measured by a Novel Real-Time Polymerase Chain Reaction Assay, Across the Proximal Promoter Region of the *IL-2* Gene," 2001, Journal of Immunology, vol. 167, 4494-4503.
Ronai, D. et al. Detection of chromatin-associated single-stranded DNA in regions targeted for somatic hypermutation. J. Exp. Med., vol. 204, No. 1, Jan. 2007.
Shiokawa et al. Stage-specific expression of DNasec during B-cell development and its role in B-cell receptor-mediated apoptosis in WEHI-231 cells. Cell Death Differ., 2007, vol. 14, No. 5, pp. 992-1000. Abstract: p. 993, col. 2, last para, and p. 1000, col. 1, para 1.
Steensel et al., "Identification of in vivo DNA targets of chromatin proteins using tethered Dam methyltransferase," Nature, 2000, vol. 18, pp. 424-428.
Tanguay et al., "PCR-aided DNaseI footprinting of single copy gene sequences in permeabilized cells," 1990, 18, 5902.
Thu KL et al., "Methylated DNA Immunoprecipitation," Journal of Visualized Experiments, 2009, 23.
Tornaletti, Silvia et al., "A high-resolution analysis of chromatin structure along p53 sequences," *Molecular Carcinogenesis, Alan Liss*, New York, NY, vol. 17, No. 4, pp. 192-201 (Dec. 1, 1996).
Wojdacz et al., "Methylation-sensitive high resolution melting (MS-HRM): a new approach for sensitive and high-throughput assessment of methylation," 2007, Nocleic Acids Research, vol. 35, No. 6, e41.
Yoon, YS et al. Poly(ADP-ribosylation of histone H1 correlates with internucleosomal DNA fragmentation during apoptosis. JBC, vol. 271, No. 15, pp. 9120-9134, 1996.
Zaret, K.S., "In vivo analysis of chromatin structure," *Methods in Enzymology, Lnkd-Pubmed*, vol. 304, pp. 612-626 (1999).
Zhang et al., "In situ nucleoprotein structure at the SV40 major late promoter: melted and wrapped DNA flank the start site," 1989, Genes and Development, 3, 1814-1822.
Zimmermann et al., "The chromatin structure of the lysozyme GAS41 origin of DNA replication changes during the cell cycle," 2007, Biol. Res., 40, 185-192.
US Final Office Action dated Aug. 23, 2016 issued in U.S. Appl. No. 13/396,496.
US Office Action dated Aug. 10, 2016 issued in U.S. Appl. No. 13/229,132.
"Epigenetic Regulation," *Innovative & Quality Tools for Epigenetics Research and DNA/RNA Purification, The Epigenetics Company*, Printed on Aug. 17, 2016, 3pp.
"Heterochromatin, from Chromosome to Protein," *Atlas of Genetics and Cytogenetics in Oncology and Haematology*, Indexed on Aug. 9, 2016, Printed on Aug. 17, 2016, 14pp.
Mathieu et al., (2002) "Methylation of a euchromatin-heterochromatin transition region in *Arabidopsis thaliana* chromosome 5 left arm," *Chromosome Research*, 10:455-466.
Chinese Office Action [The Details of the Reexamination Notification], dated Sep. 2, 2016, issued in Application No. CN 201280038451.3.
European Communication under Rule 71(3) EPC, Intention to grant, dated Jul. 21, 2016 issued in Application No. EP 12 705 595.2.
Decision to Grant a European patent dated Nov. 17, 2016 issued in Application No. EP 12 705 595.2.
European Communication under Rule 71(3) EPC, Intention to grant, dated Oct. 6, 2015 issued in Application No. EP 11 824 173.6.
Decision to Grant a European patent dated Mar. 10, 2016 issued in Application No. EP 11 824 173.6.
European Communication under Rule 71(3) EPC, Intention to grant, dated Mar. 15, 2017 issued in Application No. EP 11 824 170.2.
European Communication under Rule 71(3) EPC, Intention to grant, dated Feb. 6, 2017 issued in Application No. EP 12 819 299.4.
Japanese Decision to Grant a Patent [no translation] dated Jan. 7, 2016 issued in Application No. JP 2013-528327.
Japanese Patent No. 5871933 B2 issued Jan. 22, 2016, (Patent Application No. JP 2013-528327), English translation of Allowed Claims, 3pp.
Japanese Decision to Grant a Patent [no translation] dated Apr. 4, 2016 issued in Application No. JP 2013-528325.
Japanese Patent No. 5917519 B2 issued Apr. 15, 2016, (Patent Application No. JP 2013-528325), English translation of Allowed Claims, 5pp.
U.S. Appl. No. 15/427,845, filed Feb. 8, 2017, Okino et al.
U.S. Appl. No. 15/411,855, filed Jan. 20, 2017, Okino et al.
U.S. Restriction Requirement dated Apr. 25, 2017 issued in U.S. Appl. No. 15/411,855.
U.S. Office Action dated Jun. 2, 2017 issued in U.S. Appl. No. 15/427,845.
Canadian Examination Report, dated May 15, 2017, issued in Application No. CA 2,810,520.

\* cited by examiner

Kidney, 50 ng DNA

Brain, 20 ng DNA

FILTERING SMALL NUCLEIC ACIDS USING PERMEABILIZED CELLS

CROSS-REFERENCE TO RELATED PATENT APPLICATIONS

The present patent application is a continuation of U.S. application Ser. No. 13/565,464, filed Aug. 2, 2012, which claims benefit of priority to US Provisional Patent Application Nos. 61/514,711, filed Aug. 3, 2011 and 61/570,581, filed Dec. 14, 2011, each of which are incorporated by reference.

REFERENCE TO A "SEQUENCE LISTING" SUBMITTED AS AN ASCII TEXT FILE

The Sequence Listing written in file SEQTXT 94260-906219.txt, created on Apr. 18, 2014, 708 bytes bytes, machine format IBM-PC, MS-Windows operating system, is hereby incorporated by reference in its entirety for all purposes.

BACKGROUND OF THE INVENTION

Chromatin is classified into two main groups, euchromatin, where the DNA is loosely packaged, accessible and generally, but not always, transcriptionally competent, and heterochromatin, where the DNA is tightly packaged, inaccessible and generally, but not always, transcriptionally silent.

Epigenetics controls at least some of the transition between these two chromatin states. There are at least two main epigenetic events: DNA methylation and histone modification. These events affect how the DNA is packaged and whether the DNA is active or silent with respect to transcription.

BRIEF SUMMARY OF THE INVENTION

The present invention provides, e.g., methods of separating DNA accessible to a DNA cleaving agent in a permeabilized cell from DNA inaccessible to the DNA cleaving agent. In some embodiments, the method comprises: permeabilizing a cell having genomic DNA, thereby generating a permeabilized cell; introducing a DNA cleaving agent into the permeabilized cell having genomic DNA under conditions such that the DNA cleaving agent cleaves the genomic DNA in the cell, thereby generating cleaved DNA; and separating cleaved DNA that diffuses out of the intact permeabilized cell from the cell.

In some embodiments, the method further comprises introducing a DNA modifying agent into the permeabilized cell such that the DNA modifying agent modifies the genomic DNA in the cell. In some embodiments, the DNA modifying agent and the DNA cleaving agent are introduced simultaneously or the DNA modifying agent is introduced before the DNA cleaving agent is introduced. In some embodiments, the DNA cleaving agent is DNase I or micrococcal nuclease. In some embodiments, the DNA modifying agent adds modifications to at least some recognition sequences of the DNA cleaving agent, and the DNA cleaving agent does not cleave recognition sequences with the modification. In some embodiments, the DNA modifying agent adds modifications to at least some recognition sequences of the DNA cleaving agent, and the DNA cleaving agent cleaves recognition sequences with the modification and does not cleave recognition sequences lacking the modification.

In some embodiments, the DNA modifying agent is a DNA methyltransferase. In some embodiments, the DNA modifying agent is introduced after the DNA cleaving agent is introduced.

In some embodiments, the permeabilizing and the introducing occur simultaneously.

In some embodiments, the method further comprises isolating the cleaved DNA.

In some embodiments, the method further comprises isolating DNA remaining in the intact cell following the separating.

In some embodiments, the cell is permeabilized with a permeabilization agent. In some embodiments, the cell is permeabilized by electroporation or biolistics. In some embodiments, the permeabilization agent is a lysolipid or a nonionic detergent.

In some embodiments, the DNA cleaving agent comprises a DNase. In some embodiments, the DNA cleaving agent is DNase I or micrococcal nuclease.

In some embodiments, the DNA cleaving agent comprises a restriction enzyme. In some embodiments, the restriction enzyme is a methylation sensing restriction enzyme. In some embodiments, the restriction enzyme is a $N^6$-methyl adenosine sensing restriction enzyme. In some embodiments, the restriction enzyme is a methyl cytosine sensing restriction enzyme. In some embodiments, the restriction enzyme is a 5-hydroxymethyl cytosine-sensing restriction enzyme. In some embodiments, the restriction enzyme cleaves a recognition sequence comprising a 5'-hydroxymethylcytosine.

In some embodiments, the DNA cleaving agent comprises a DNA cleaving polypeptide fused to a heterologous DNA-recognition polypeptide.

In some embodiments, the DNA cleaving agent comprises a DNA cleaving polypeptide fused to a heterologous protein-recognition polypeptide.

In some embodiments, the isolating comprises affinity purifying the DNA. In some embodiments, the affinity purifying comprises immunoprecipitating. In some embodiments, the DNA is affinity purified by binding an affinity agent to a protein associated with the DNA, thereby purifying the protein and DNA associated with the protein. In some embodiments, the affinity agent is an antibody. In some embodiments, the affinity agent is linked to a solid support. In some embodiments, the protein associated with the DNA is a histone, a modified histone (modified (e.g., methylated) or not), a transcription factor, an RNA polymerase or a TATA box-binding protein (TBP).

In some embodiments, the isolated DNA is from about 50 bp to about 10 kb.

In some embodiments, the method further comprises analyzing the separated DNA. In some embodiments, the analyzing comprises nucleotide sequencing the separated DNA. In some embodiments, the nucleotide sequencing further detects DNA modifications. In some embodiments, the analyzing comprises an amplification reaction. In some embodiments, the analyzing comprises nucleic acid hybridization. In some embodiments, two or more nucleic acids are associated with one or more proteins and the analyzing comprises ligating the two or more nucleic acids.

In some embodiments, the isolated DNA is associated with one or more protein. In some embodiments, the method further comprises analyzing the one or more protein associated with the isolated DNA.

In some embodiments, the isolated DNA is associated with one or more RNA. In some embodiments, the method further comprises analyzing the one or more RNA associated with the isolated DNA.

In some embodiments, the separating comprises centrifuging and/or filtering the permeabilized cell thereby separating a solution containing the cleaved DNA from the cell. In some embodiments, a DNA modification agent was introduced into the permeabilized cell and the analyzing comprises determining the presence or absence of modifications in the isolated DNA.

The present invention also provides for kits, e.g., comprising one or more reagent as described herein for use with the methods described herein. In some embodiments, the kit comprises a DNA modifying agent and/or a DNA cleaving agent; a cell permeabilization agent; and an affinity agent that specifically binds to a DNA-binding protein.

In some embodiments, the DNA cleaving agent comprises a DNase or a restriction enzyme or a DNA cleaving polypeptide fused to a heterologous DNA-recognition polypeptide. In some embodiments, the DNA modifying agent is a DNA methyltransferase. In some embodiments, the permeabilization agent is a lysolipid or a nonionic detergent. In some embodiments, the affinity agent specifically binds to a histone, an RNA polymerase, a transcription factor, or a TATA box-binding protein (TBP). In some embodiments, the affinity agent is linked to a solid support. In some embodiments, the solid support is a bead or particle. In some embodiments, the bead or particle is magnetic.

DEFINITIONS

"Permeabilizing," a cell membrane, as used herein, refers to reducing the integrity of a cell membrane, thereby allowing smaller genomic DNA fragments or protein-DNA/histone DNA complexes to diffuse from the cells, and optionally to allow for entry of a DNA cleaving and/or modifying agent, or other enzyme proteins, antibodies or chimeric proteins into the cell. A cell with a permeabilized cell membrane will generally retain the cell membrane such that the cell's structure remains substantially intact. A cell with a permeabilized membrane is not a "lysed" cell, for example as occurs in standard DNA purification techniques. In contrast, "disrupting" a cell membrane, as used herein, refers to reducing the integrity of a cell membrane such that the cell's structure does not remain intact (e.g., such as during cell lysis).

A "DNA modifying agent," as used herein, refers to a molecule that alters DNA in a detectable manner. Exemplary modifications include DNA cleavage, DNA nicking, or introduction or removal of chemical moieties from the DNA (generally wherein the introduction or removal does not directly result in cleavage of the DNA). DNA modifying agents include, but are not limited to, DNA methyltransferases.

A "DNA region," as used herein, refers to a target sequence of interest within genomic DNA. The DNA region can be of any length that is of interest and that is accessible by the DNA modifying agent being used. In some embodiments, the DNA region can include a single base pair, but can also be a short segment of sequence within genomic DNA (e.g., 2-100, 2-500, 50-500 bp) or a larger segment (e.g., 100-10,000, 100-1000, or 1000-5000 bp). The amount of DNA in a DNA region is sometimes determined by the amount of sequence to be amplified in a PCR reaction (i.e., between two primers). For example, standard PCR reactions generally can amplify between about 35 to 5000 base pairs.

A different "extent" of modifications refers to a different number (actual or relative) of modified copies of one or more DNA regions between samples or between two or more DNA regions in one or more samples. For example, if 100 copies of two DNA regions (designated for convenience as "region A" and "region B") are each present in chromosomal DNA in a cell, an example of modification to a different extent would be if 10 copies of region A were modified whereas 70 copies of region B were modified.

The terms "oligonucleotide" or "polynucleotide" or "nucleic acid" interchangeably refer to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™), and the like. In certain applications, the nucleic acid can be a polymer that includes multiple monomer types, e.g., both RNA and DNA subunits.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) Tetrahedron 49(10):1925 and the references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110:4470; and Pauwels et al. (1986) Chemica Scripta 26:1419), phosphorothioate (Mag et al. (1991) Nucleic Acids Res. 19:1437 and U.S. Pat. No. 5,644,048), phosphorodithioate (Briu et al. (1989) J. Am. Chem. Soc. 111:2321), O-methylphophoroamidite linkages (Eckstein, Oligonucleotides and Analogues: A Practical Approach, Oxford University Press (1992)), and peptide nucleic acid backbones and linkages (Egholm (1992) J. Am. Chem. Soc. 114:1895; Meier et al. (1992) Chem. Int. Ed. Engl. 31:1008; Nielsen (1993) Nature 365:566; and Carlsson et al. (1996) Nature 380:207), which references are each incorporated by reference. Other analog nucleic acids include those with positively charged backbones (Denpcy et al. (1995) Proc. Natl. Acad. Sci. USA 92:6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (Jenkins et al. (1995) Chem. Soc. Rev. pp169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

"Accessibility" of a DNA region to a DNA modifying agent, as used herein, refers to the ability of a particular DNA region in a chromosome of a cell to be contacted and modified by a particular DNA modifying agent. Without intending to limit the scope of the invention, it is believed that the particular chromatin structure comprising the DNA region will affect the ability of a DNA modifying agent to modify the particular DNA region. For example, the DNA region may be wrapped around histone proteins and further may have additional nucleosomal structure that prevents, or reduces access of, the DNA modifying agent to the DNA region of interest.

The phrase "specifically (or selectively) binds" refers to a binding reaction that is determinative of the presence of the target (e.g., a target protein) in a heterogeneous population of proteins and other biologics. For example, under immunoassay conditions, antibodies or other protein recognition polypeptides bind to a particular protein at least two times background and do not substantially bind in a significant amount to other proteins present in the sample. Typically a specific or selective reaction will be at least twice background signal or noise and more typically more than 10 to 100 times background.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined by, e.g., Kabat et al. (Kabat et al., Sequences of Proteins of Immunological Interest, Fifth Edition, U.S. Department of Health and Human Services, U.S. Government Printing Office (1991)).

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies can exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see FUNDAMENTAL IMMUNOLOGY (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

DETAILED DESCRIPTION OF THE INVENTION

I. Introduction

Figure 1:
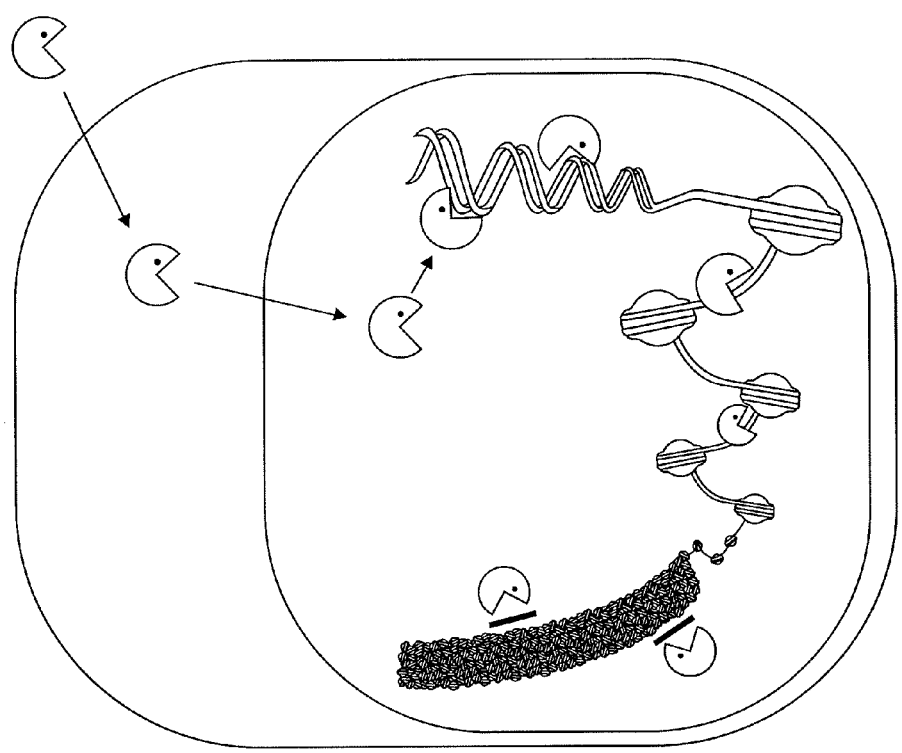
FIG. 1 is a illustration showing DNA cleaving agents (appearing as eating faces) entering a permeabilized cell. For example, the cells can be treated with a buffer that contains a permeabilization agent and a DNA cleaving agent. The cleaving agent enters the permeabilized cell and digests genomic DNA (chromatin) that is in an open/accessible conformation. Inaccessible chromatin is not digested.
Figure 2:
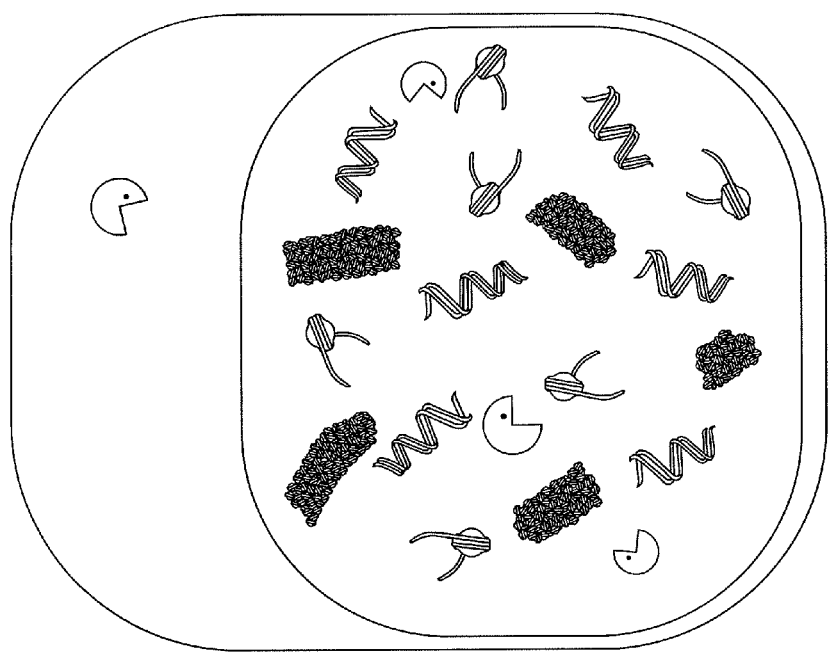
FIG. 2 is a schematic representation of DNA inside the cell following digestion. The accessible chromatin is in small fragments and the inaccessible chromatin is, relatively, much larger.

The invention allows for analysis of chromatin structure by introducing a DNA cleaving agent into a permeabilized cell such that the DNA cleaving agent cleaves genomic DNA within the cell, and then separating DNA fragments that diffuse out of the permeabilized cell from the cell itself. Without intending to limit the scope of the invention, it is believed that generally smaller fragments will diffuse out from the permeabilized cell and that those smaller fragments represent genomic DNA regions in which the DNA cleaving agent had greater access compared to other regions of genomic DNA. It is believed that accessibility of the DNA cleaving agent reflects the chromatin state of regions of genomic DNA. The smaller fragments, which generally diffuse out from the cell, represent regions that are more accessible to the DNA cleaving agent than larger fragments, which generally do not diffuse from the cell. By analyzing the smaller fragments that have diffused from the permeabilized cell, or the larger fragments that do not diffuse, or both, one can measure DNA cleaving accessibility, and thus indirectly, chromatin structure, for DNA regions of interest.

The varying accessibility of the DNA can reflect chromatin structure of the genomic DNA. For example, in some embodiments, DNA regions that are more accessible to DNA cleaving agents are likely in more "loose" chromatin structures. Measurement of the chromatin state can provide useful information regarding the biological state of a cell. For example, in some embodiments, the chromatin state of one or more DNA regions can provide diagnostic, prognostic, or other medical information. As a non-limiting example, chromatin states can change as a normal cell progresses into cancer.

II. General Method

In one aspect, one or more DNA cleaving agent is introduced into a cell under conditions such that genomic DNA is cleaved within the cell. Smaller cleaved fragments are then allowed to diffuse from the permeabilized cell and the diffused DNA can then be separated from the permeabilized cells, thereby allowing analysis of the diffused DNA and/or the DNA remaining in the permeabilized cell.

Permabilization of the cell can occur before, during, or after the the DNA cleaving agent is introduced into the cell. An exogenous DNA cleaving agent will generally be introduced following or simultaneous with permeabilization so that the DNA cleaving agent can enter the cell via "holes" in the cell generated by the permeabilizing step. In these embodiments, the permeabilized cells can be incubated in a sufficient concentration of the DNA cleaving agent to allow for the DNA cleaving agent to enter the cell. Alternatively, the DNA cleaving agent can be expressed in (e.g., from an inducible promoter), or otherwise introduced into (e.g., via electroporation), the cell prior to the permeabilization. In these latter embodiments, permeabilization is not used to assist introduction of the DNA cleaving agents into the cell, but instead only provide exits by which the smaller cleaved DNA fragments can diffuse.

III. Permeabilizing Cells

Cell membranes can be permeabilized or disrupted in any way known in the art. The methods of permeabilizing or disrupting the cell membrane do not disrupt the structure of the genomic DNA of the cell such that nucleosomal or chromatin structure is destroyed.

In some embodiments, the cell membrane is contacted with an agent that permeabilizes the cell membrane. Lysolipids are an exemplary class of agents that permeabilize cell membranes. Exemplary lysolipids include, but are not limited to, lysophosphatidylcholine (also known in the art as lysolecithin) or monopalmitoylphosphatidylcholine. A variety of lysolipids are also described in, e.g., WO/2003/052095. The precise concentration of the agent will depend on the agent used as well, in some embodiments, to the cell to be permeabilized. As an example, in some embodiments, 0.25, 0.5%, 0.75 or 1% (or a concentration between 0.25% and 1%) of lysolecithin (w/v) is used.

Non ionic detergents are an exemplary class of agents that disrupt cell membranes. Exemplary nonionic detergents, include but are not limited to, NP40, Tween 20 and Triton X-100. The precise concentration of the agent will depend on the non ionic detergent used as well, in some embodiments, to the cell to be permeabilized.

Alternatively, electroporation or biolistic methods can be used to permeabilize a cell membrane such that a DNA cleaving agent is introduced into the cell and can thus contact the genomic DNA. A wide variety of electroporation methods are well known and can be adapted for delivery of DNA modifying agents as described herein. Exemplary electroporation methods include, but are not limited to, those described in WO/2000/062855. Biolistic methods include but are not limited to those described in U.S. Pat. No. 5,179,022.

IV. DNA Cleaving Agents

Following, simultaneously with, or after permeabilization, a DNA cleaving agent is introduced into the cell such that the agent contacts and cleaves accessible genomic DNA in the cell. A DNA cleaving agent is any agent that introduces a double-stranded DNA break in DNA. A wide variety of DNA cleaving agents can be used according to the present invention. DNA cleaving agents can be, for example, a protein with double stranded DNA cleaving activity or a chemical having sufficient steric hindrance such that differences in accessibility occur within genomic DNA in the cell.

In some embodiments, the DNA cleaving agent(s) are contacted to the permeabilized cells following removal of the permeabilizing agent, optionally with a change of the buffer. Alternatively, in some embodiments, the DNA cleaving agent is contacted to the genomic DNA without one or more intervening steps (e.g., without an exchange of buffers, washing of the cells, etc.). This latter approach can be convenient for reducing the amount of labor and time necessary and also removes a potential source of error and contamination in the assay.

The quantity of DNA cleaving agent used, as well as the time of the reaction, will depend on the agent used. Those of skill in the art will appreciate how to adjust conditions depending on the agent used. Generally, the conditions of the DNA cleaving step are adjusted such that a "complete" digestion is not achieved. Thus, for example, in some embodiments, the conditions of the cleaving step is set such that the positive control—i.e., the control where cleavage sites are accessible—occurs at a high level but less than 100%, e.g., between 50-60%, 60-70%, 70-80%, 80-95%, 80-99%, 85-95%, 90-98%, etc.

In some embodiments, the DNA cleaving agent cleaves modified DNA, but not unmodified DNA. In other embodiments, the DNA cleaving agent cleaves unmodified DNA but not modified DNA. In some of these embodiments, the DNA cleaving agent is used in combination with a DNA modifying agent (discussed further herein), thereby detecting accessible.

A. Restriction Enzymes

In some embodiments, the DNA cleaving agent is a restriction enzyme. A wide variety of restriction enzymes are known and can be used in the present invention.

Any type of restriction enzyme can be used. Type I enzymes cut DNA at random far from their recognition sequences. Type II enzymes cut DNA at defined positions close to or within their recognition sequences. Some Type II enzymes cleave DNA within their recognition sequences. Type II-S enzymes cleave outside of their recognition sequence to one side. The third major kind of type II enzyme, more properly referred to as "type IV," cleave outside of their recognition sequences. For example, those that recognize continuous sequences (e.g., AcuI: CTGAAG) cleave on just one side; those that recognize discontinuous sequences (e.g., BcgI: CGANNNNNNTGC; SEQ ID NO:1) cleave on both sides releasing a small fragment containing the recognition sequence. Type III cleave outside of their recognition sequences and require two such sequences in opposite orientations within the same DNA molecule to accomplish cleavage.

The methods of the invention can be adapted for use with any type of restriction enzyme or other DNA cleaving enzyme. In some embodiments, the enzyme cleaves relatively close (e.g., within 5, 10, or 20 base pairs) of the recognition sequence. Such enzymes can be of particular use in assaying chromatin structure as the span of DNA that must be accessible to achieve cutting is larger than the recognition sequence itself and thus may involve a wider span of DNA that is not in a "tight" chromatin structure.

In some embodiments, more than one (e.g., two, three, four, etc.) restriction enzymes are used. Combinations of enzymes can involve combinations of enzymes all from one type or can be mixes of different types.

In some embodiments, the restriction enzyme is a modification-sensing restriction enzyme, meaning that the restriction enzyme is either modification-dependent (i.e., cleaving in the presence but not absence of modifications in the recognition sequence) or methylation-sensitive (i.e., cleaving in the absence but not presence of modifications in the recognition sequence). An exemplary modification is, e.g., DNA methylation or DNA acetylation.

DNA methylation can occur in several different types, including at the $N^6$ position of adenosine and at the $C^4$ and $C^5$ positions of cytosine (which can be methylation of hydroxymethylation). A number of methyl-adenosine sensing and methyl-cytosine sensing restriction enzymes are known. Exemplary $N^6$-methyl-adenosine sensitive restriction enzymes include, e.g., DpnII. Exemplary $N^6$-methyl-adenosine dependent restriction enzymes include, e.g., DpnII. Exemplary methyl-cytosine sensitive restriction enzymes include, e.g., MspI and GlaI. Exemplary methyl-cytosine dependent restriction enzymes include, e.g., MspJI.

In some embodiments, the restriction enzyme is a hydroxymethyl cytosine sensing restriction enzyme. For example, PvuRTS1 is a hydroxymethyl cytosine-dependent restriction enzyme (Janosi et al., *J. Mol. Biol.* 242:45-61 (1994)) and can be used as the DNA cleaving agent, thereby identifying accessible or inaccessible regions having or lacking hydroxymethyl cytosine.

B. DNases

In some embodiments, an enzyme that cleaves DNA in a sequence non-specific manner is used as a DNA cleaving agent. Thus, in some embodiments, the DNA cleaving agent is a sequence non-specific endonuclease (also referred to herein as a "DNase").

Any sequence non-specific endonuclease (e.g., micrococcal nuclease (MNase) or any of DNase I, II, III, IV, V, VI, VII) can be used according to the present invention. For example, any DNase, including but not limited to, DNase I and MNase can be used. MNases can induce double stand breaks within nucleosome linker regions, but only single-strand breaks within the nucleosome itself. DNases used can include naturally occurring DNases as well as modified DNases. An example of a modified DNase is TURBO DNase (Ambion), which includes mutations that allow for "hyperactivity" and salt tolerance. Exemplary DNases, include but are not limited, to Bovine Pancreatic DNase I (available from, e.g., New England Biolabs).

C. Fusion Proteins

In some embodiments, the DNA cleaving or modifying agents are fused or otherwise linked to a heterologous double-stranded sequence-non-specific nucleic acid binding domain (e.g., a DNA binding domain), a heterologous sequence-specific nucleic acid binding (i.e., a "DNA-recognition") polypeptide, or a heterologous protein binding (i.e., a "protein-recognition") polypeptide. In cases where the DNA cleaving or modifying agent is a polypeptide, the DNA cleaving or modifying agent and the heterologous polypeptide can be generated as a single polypeptide, synthesized, for example, as a protein fusion via recombinant DNA technology.

A double-stranded sequence-non-specific nucleic acid binding domain is a protein or defined region of a protein that binds to double-stranded nucleic acid in a sequence-independent manner, i.e., binding does not exhibit a gross preference for a particular sequence. A double-stranded sequence-non-specific nucleic acid binding domain fusion can have improved activity compared to the DNA cleaving or modifying agent lacking the double-stranded sequence-non-specific nucleic acid binding domain. In some embodiments, double-stranded nucleic acid binding proteins exhibit a 10-fold or higher affinity for double-stranded versus single-stranded nucleic acids. The double-stranded nucleic acid binding proteins in some embodiments of the invention are thermostable. Examples of such proteins include, but are not limited to, the Archaeal small basic DNA binding proteins Sac7d and Sso7d (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998), Archael HMf-like proteins (see, e.g., Starich et al., *J. Molec. Biol.* 255:187-203, 1996; Sandman et al., *Gene* 150:207-208, 1994), and PCNA homologs (see, e.g., Cann et al., *J. Bacteriology* 181:6591-6599, 1999; Shamoo and Steitz, *Cell:*99, 155-166, 1999; De Felice et al., *J. Molec. Biol.* 291, 47-57, 1999; and Zhang et al., *Biochemistry* 34:10703-10712, 1995). See also European Patent 1283875B1 for addition information regarding DNA binding domains.

Sso7d and Sac7d are small (about 7,000 kd MW), basic chromosomal proteins from the hyperthermophilic archaeabacteria *Sulfolobus solfataricus* and *S. acidocaldarius*, respectively. These proteins are lysine-rich and have high thermal, acid and chemical stability. They bind DNA in a sequence-independent manner and when bound, increase the $T_M$ of DNA by up to 40° C. under some conditions (McAfee et al., *Biochemistry* 34:10063-10077, 1995). These proteins and their homologs are typically believed to be involved in stabilizing genomic DNA at elevated temperatures.

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to Taq DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

Those of skill in the art will recognize that other double-stranded sequence-non-specific nucleic acid binding domain are known in the art and can also be used as described herein.

The heterologous sequence-specific nucleic acid binding (i.e., a "DNA-recognition") polypeptide allows for targeting of the DNA cleaving or modifying agent to particular DNA sequences in the cell, thereby allowing one to assay the accessibility of specific DNA sequences in the genome. A wide variety of sequence specific DNA binding polypeptides and domains are known and can be used as fusion partners with the DNA cleaving or modifying agent as desired. Exemplary sequence-specific DNA binding polypeptides include, but are not limited to, zinc finger domains, TAL domains, etc.

The heterologous protein-recognition polypeptide (i.e. a polypeptide that specifically binds a particular protein or class of proteins) allows for targeting of the DNA cleaving or modifying agent to particular protein associated with genomic DNA, thereby targeting genomic DNA that is both accessible to the agent and in proximity to the particular targeted protein. A wide variety of protein-recognition polypeptides and domains are known and can be used as fusion partners with the DNA cleaving or modifying agent as desired. Exemplary protein-recognition polypeptides include, but are not limited to, antibodies.

V. DNA Modifying Agents

In addition to the DNA cleaving agents, one or more DNA modifying agents can also be introduced into the permeabilized cells. DNA modifying agents generate a covalent modification to the DNA. In some cases, the DNA modifying agent is introduced before or simultaneously with the DNA cleaving agent. In some embodiments, the DNA modifying agent is introduced to the cell simultaneously with the permeabilizing agent and subsequently, the DNA cleaving agent is introduced into the cell. In some embodiments, the DNA cleaving agent is a modification-sensing enzyme, wherein the DNA cleaving agent only cleaves modified DNA or DNA containing a modified recognition sequence, or alternatively, only cleaves unmodified DNA or DNA containing an unmodified recognition sequence.

For example, in some embodiments, the DNA modifying agents of the invention are methyltransferases. A variety of methyltransferases are known in the art and can be used in the invention. In some embodiments, the methyltransferase used adds a methyl moiety to adenosine in DNA. Examples of such methyltransferases include, but are not limited to, DAM methyltransferase. Because adenosine is not methylated in eukaryotic cells, the presence of a methylated adenosine in a particular DNA region following treatment of the cell with an adenosine methyltransferase (e.g., a DAM methyltransferase or other methyltransferase with similar activity) indicates that it was able to access the DNA region. Adenosine methylation can be detected, for example, using as a DNA cleaving agent a restriction enzyme whose recognition sequence includes a methylated adenosine. An example of such an enzyme includes, but is not limited to, DpnI. Cutting by the restriction enzyme can be detected and quantified by measuring the identity and amount of DNA fragments that diffuse from the cells.

In some embodiments, the methyltransferase methylates cytosines in GC sequences. Examples of such methyltransferases include but are not limited to MCviPI. See, e.g., Xu et al., *Nuc. Acids Res.* 26(17): 3961-3966 (1998). Because GC sequences are not methylated in eukaryotic cells, the presence of a methylated GC sequence in a particular DNA region indicates that the DNA modifying agent (i.e., a methyltransferase that methylates cytosines in GC sequences) was able to access the DNA region. Methylated GC sequences can be identified using any number of techniques. In some embodiments, the method for detecting methylated GC sequences comprises bisulfite conversion. Bisulfite conversion involves contacting the DNA with a sufficient amount of bisulfite to convert unmethylated cytosines to uracil. Methylated cytosines are not converted. Thus, DNA regions containing a GC sequence can be contacted with a methyltransferase that methylates cytosines in GC sequences, isolated, and then contacted with bisulfite. If the C in the GC sequence is not methylated, the C will be converted to U (or T if subsequently amplified), whereas a methylated C will remain a C. Any number of methods, including but not limited to, nucleotide sequencing and methods involving primer extension or primer-based amplification and/or methylation-sensitive restriction digests can be used to detect the presence or absence of a bisulfite converted C (e.g., MSnuPE, MSP or Methyllight, high resolution melt analysis; pyrosequencing, etc.). See, e.g., Fraga, et al., *Biotechniques* 33:632, 634, and 636-649 (2002); El-Maarri O Adv Exp Med Biol 544:197-204 (2003); Laird, *Nat Rev Cancer* 3:253-266 (2003); and Callinan, *Hum Mol Genet* 15 Spec No 1:R95-101 (2006).

In some embodiments, the methyltransferase methylates cytosines in CG (also known as "CpG") sequences. Examples of such methyltransferases include but are not limited to M.SssI. Use of such methyltransferases will generally be limited to use for those DNA regions that are not typically methylated. This is because CG sequences are endogenously methylated in eukaryotic cells and thus it is not generally possible to assume that a CG sequence is methylated by the modifying agent rather than an endogenous methyltransferase except in such DNA regions where methylation is rare. As for GC sequences, methylation of CG sequences can be detected by any number of methods, including methods involving bisulfite conversion.

In some embodiments, the DNA modifying agent comprises a DNA modifying chemical. As most DNA modifying chemicals are relatively small compared to chromatin, use of DNA modifying chemicals without a fusion partner may not be effective in circumstances in which the chemical is introduced into the cell because there will be little if any difference in the extent of accessibility of different DNA regions. Therefore, in some embodiments, the DNA modifying agent comprises a molecule having steric hindrance linked to a DNA modifying chemical. The molecule having steric hindrance can be any protein or other molecule that results in differential accessibility of the DNA modifying agent depending on chromatin structure. This can be tested, for example, by comparing results to those using a DNase or restriction enzyme as described herein.

In some embodiments, the molecule having steric hindrance will be at least 5, 7, 10, or 15 kD in size. Those of skill in the art will likely find it convenient to use a polypeptide as the molecule with steric hindrance. Any polypeptide can be used that does not significantly interfere with the DNA modifying agent's ability to modify DNA. In some embodiments, the polypeptide is a double-stranded sequence-non-specific nucleic acid binding domain as discussed in further detail herein.

The DNA modifying chemicals of the present invention can be linked directly to the molecule having steric hindrance or via a linker. A variety of homo and hetero bifunctional linkers are known and can be used for this purpose.

VI. Separating Diffused DNA from Permeabilized Cells

Figure 4:
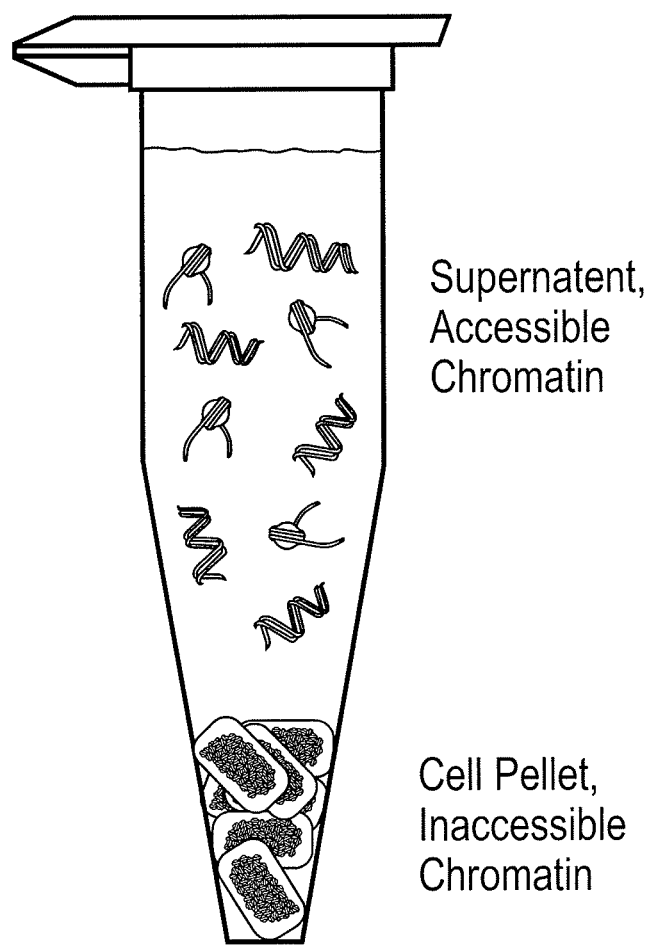
FIG. 4 illustrates an embodiment of the invention in which permeabilized and nuclease-treated cells are centrifuged. The cells, containing inaccessible chromatin, will be in the pellet and the supernatant will contain accessible DNA that is relatively small in size.

Following DNA cleavage in the cell and cell permeabilization, the smaller DNA fragments and/or protein/DNA complexes are allowed to diffuse from the cell. After an appropriate amount of time has elapsed for diffusion to occur, the diffused DNA and/or protein/DNA complexes are subsequently separated from the cell. Separation can readily be achieved, for example, by centrifuging the cells following diffusion, thereby pelleting the intact permeabilized cells. See, e.g., FIG. 4. In some embodiments, separation will comprise one or more filtrations using filters that block cell passage but allow DNA passage.

The diffused DNA can be any size, but as noted herein, is expected to be smaller than DNA retained in the permeabilized cell. As DNA retained in the cell will generally be 10,000 base pairs or larger, in some embodiments, the diffused DNA is generally less than 10,000 bp, e.g., less than 5,000 bp, less than 3,000 bp, less than 1,000 bp, e.g., between 5-1,000 bp, 50-500, 50-1000 bp, 50-5,000 bp, or 50-10,000 bp.

The supernatant containing the diffused DNA can be removed, and optionally the diffused DNA can be further purified.

In some embodiments, the DNA remaining in the permeabilized cells is purified from the cells following separation from the diffused DNA. Any type of DNA purification from the cells can be used as desired. The DNA remaining in the cell represents DNA that was relatively inaccessible to the DNA cleaving agent and thus can be analyzed to determine the identity of DNA regions that are inaccessible. In some embodiments, diffused and non-diffused DNA are both analyzed and optionally compared, for example as a control to each other.

In some embodiments, the non-diffused genomic DNA in the permeabilized cell is purified according to any method available. Essentially any DNA purification procedure can be used so long as it results in DNA of acceptable purity for the subsequent analysis step(s). For example, standard cell lysis reagents can be used to lyse cells. Optionally a protease (including but not limited to proteinase K) can be used. DNA can be isolated from the mixture as is known in the art. In some embodiments, phenol/chloroform extractions are used and the DNA can be subsequently precipitated (e.g., by ethanol) and purified. In some embodiments, RNA is removed or degraded (e.g., with an RNase or with use of a DNA purification column), if desired. Optionally, genomic DNA is amplified or otherwise detected directly from the cell lysate without an intermediate purification step.

VII. Analyzing DNA and/or Protein

DNA and proteins that diffuse from the permeabilized cell can be analyzed in any way useful to the user. Thus, the following is not intended to be an exhaustive listing. Analysis can include, but need not be limited to, determining the identity and/or quantity of a particular molecule (e.g., a DNA sequence or protein). Analysis can also include, for example, cloning the DNA, sequencing the DNA or analyzing the DNA using microarrays.

It is believed that both DNA and chromatin protein or other DNA binding proteins in association with the DNA can diffuse from the cells following cleavage and permeabilization. Similarly, it is believed that in some embodiments, RNA in association with the DNA can diffuse from the cells following cleavage and permeabilization. In some embodiments, the diffused DNA is analyzed. In some embodiments, the associated protein is analyzed. In some embodiments, both the diffused DNA and associated proteins are analyzed. In some embodiments, the RNA is analyzed. In some embodiments, the DNA and RNA are analyzed. Moreover, as explained herein, in some embodiments, the DNA that did not diffuse from the cell can be purified from the cell and analyzed. This DNA will in some embodiments provide a control or "mirror image" result from the diffused DNA. Thus, unless indicated otherwise, to the extent the following discussion refers to "DNA," it refers equally to diffused DNA or DNA that did not diffuse and was isolated from the permeabilized cells after the diffused DNA was separated from the cell(s).

In some embodiments, prior to DNA analysis, the DNA (i.e., enriched from DNA fragments leaked, and optionally separated, from the permeabilized cell) is enriched for one or more particular DNA sequences, for example, by affinity purifying particular DNA sequences using a nucleic acid probe (optionally linked to a solid support (e.g., a bead)) under appropriate hybridization conditions. In other embodiments the DNA is affinity-purified using an antibody or non-antibody protein (such as, but not limited to, a transcription factor, a transcription factor protein or DNA-binding fragment thereof, or a methyl-DNA binding protein) that binds to DNA.

Figure 8:
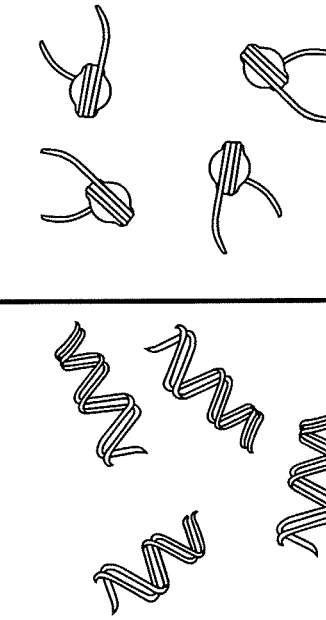
FIG. 8 illustrates various types of molecules that can be targeted to diffuse from permeabilized cells treated with a DNA cleaving agent. Each column illustrates a possible target molecule in the supernatant (depending on how the assay is performed as described further herein), some possible ways to analyze the target molecule, comparative current methods for obtaining similar information, and finally some advantages of the current method over the comparative method.

Alternatively, in situations in which there are proteins in association with the diffused DNA, DNA in association with the proteins can be further purified from other DNA by selectively binding the protein with an affinity agent that specifically binds the protein and then purifying the protein and associated DNA from other DNA not in association with the protein. See, FIG. 8. It will be appreciated that any agent having affinity (e.g., that specifically binds) with the protein can be used in this way. In some embodiments, the agent is an antibody specific for a particular protein. In other embodiments the affinity agent is a non-antibody protein. The protein associated with the DNA can be any DNA-binding protein, including but not limited to, chromatin proteins, histones (including but not limited to H3K4me histone H3. i.e., histone H3 trimethylated at lysine 4), transcription factors, RNA polymerase, and TATA box binding protein (TBP). In some embodiments, the protein and associated DNA are immunoprecipitated, thereby separating the DNA associated with the protein from other DNA. In other embodiments, the affinity agent (e.g., antibody), linked directly or indirectly to a solid support, is incubated with the supernatant of a permeabilized cell under conditions to bind the affinity agent to the target binding protein complexed with DNA fragments. The resulting complex (affinity agent, target protein, fragmented DNA) can then be separated from the supernatant, thereby purifying the target DNA binding protein and associated DNA. Any solid support can be used. In some embodiments, the solid support is a bead or particle. In some embodiments, the bead or particle is magnetic, or can be attracted to a magnet, thereby allowing for efficient purification from the supernatant when desired. If desired, the presence, absence or quantity of DNA associated with a protein can be analyzed (e.g., amplified, sequenced, detected, etc.) and optionally compared between samples, including but not limited, between diseased and healthy samples.

In some embodiments, DNA associated with proteins is analyzed by nucleotide sequencing. See, FIG. 8. For example, sequencing processes that can simultaneous detect nucleotide sequence and distinguish whether sequenced nucleotides are modified can be used. Examples of the latter type of sequencing include, but are not limited to, single-molecule real-time (SMRT) sequencing and nanopore sequencing. Results from such analyses is similar to that obtained from ChIP-Seq (see, e.g., Johnson et al., *Science* 316: 1497-1502 (2007)), but provides data only for accessible sequences, which may be advantageous in some instances as accessible chromatin is thought to be the functionally active regions of the genome.

In some embodiments, multiple (e.g., two or more) DNA fragments diffuse from the cell in a complex with one or more protein. See, FIG. 8, right column. In some embodiments, the DNA and/or proteins in the complex are analyzed. In some embodiments, these complexes are purified from the remaining DNA and then analyzed. In some embodiments, the complexes are contacted with a DNA ligase, thereby ligating the multiple DNA fragments together, which can subsequently be analyzed by any way desired (e.g., amplified, hybridized, sequenced, etc.). This analysis will provide, for example, information regarding associations and interactions of accessible chromatin regions.

DNA Analysis

In some embodiments, following isolation of DNA of interest, the DNA is cloned into a library. In some cases, one or more specific DNA sequence is isolated and/or cloned. Alternatively, the DNA is used to prepare a library (either representing diffused DNA or non-diffused DNA).

In some embodiments, subtractive libraries are generated. For example, libraries can be generated that are enriched for a diseased cell diffused or non-diffused DNA regions in the methods of the invention and subsequently subtracted with a corresponding library from a healthy cell, or vice versa, thereby generating a library of differential DNA sequences specific for the particular disease. Any diseased cell can be used, including but not limited to, cancer cells. Alternate subtractive strategies can also be employed, e.g., between different cell types, cell stages, drug treatments, etc.

Analysis can include determination of any physical characteristic of the DNA. Physical characteristics include, but are not limited to, DNA methylation, melting temperature, GC content, nucleotide sequence, and ability to hybridize to a polynucleotide or ability to be amplified. A variety of methods are known for detecting such characteristics and can be employed.

In some embodiments, the physical characteristic is DNA methylation. For example, once relatively accessible DNA has been cleaved by a DNA cleaving agent, one can isolate the remaining intact DNA (representing less accessible DNA) and can then be analyzed for methylation status. A large variety of DNA methylation detection methods are known. In some embodiments, the DNA is contacted with bisulfite, thereby converting unmethylated cytosines to uracils in the DNA. The methylation of a particular DNA region can then be determined by any number of methylation detection methods, including those discussed herein. In some embodiments, a high resolution melt assay (HRM) is employed to detect methylation status following bisulfite conversion. In this method, a DNA region is amplified following bisulfite conversion and the resulting amplicon's melting temperature is determined. Because the melting temperature will differ depending on whether the cytosines were converted by bisulfite (and subsequently copied as "T's" in the amplification reaction), melting temperature of the amplicon can be correlated to methylation content.

In some embodiments, one or more DNA sequence is amplified, for example using end point or quantitative amplification techniques (e.g., qPCR). In some embodiments, one or more specific primers are used to specifically amplify a particular sequence with in the DNA. Quantitative amplification (including, but not limited to, real-time PCR) methods allow for determination of the amount of intact copies of a DNA region, and can be used with various controls to determine the relative amount of copies of the DNA region in a sample of interest (e.g., as diffused from a permeabilized cell or not diffused from the cell), thereby indicating whether and to what extent a specific DNA region(s) is accessible.

Quantitative amplification methods (e.g., quantitative PCR or quantitative linear amplification) involve amplification of nucleic acid template, directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. However, alternative methods of amplification have been described and can also be employed, as long as the alternative methods amplify intact DNA to a greater extent than the methods amplify cleaved or degraded DNA. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002). Amplifications can be monitored in "real time."

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

In some embodiments, the nucleotide sequence of one or more DNA fragment, or a sequence thereof, is determined. For example, a genomic DNA sequence for a sample of interest can be sequenced and compared to corresponding known genomic DNA sequences in order to determine sites of DNA accessibility or inaccessibility in the sample of interest. Methods of nucleic acid sequencing are well-known in the art. Examples of sequence analysis include, but are not limited to, Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), and sequencing by hybridization (Chee et al., *Science*, 274:610-614 (1996); Drmanac et al., *Science*, 260:1649-1652 (1993); Drmanac et al., *Nature Biotech.*, 16:54-58 (1998)).

A variety of methods can be used to determine the nucleotide sequence and, if desired, the extent to which sequenced nucleotides are modified, e.g., methylated, either naturally within the cell or by an introduced DNA modifying agent. Any sequencing method known in the art can be used. In some embodiments, the sequencing method simultaneously determines the nucleotide sequence and whether sequenced nucleotides are modified. For example, as the sequencing process determines the order of nucleotides in a nucleic acid fragment, at the same time it can also distinguish between modified nucleotides (e.g., methylated nucleotides) and non-modified nucleotides (e.g., non-methylated nucleotides). Examples of sequencing processes that can simultaneous detect nucleotide sequence and distinguish whether sequenced nucleotides are modified include, but are not limited to, single-molecule real-time (SMRT) sequencing and nanopore sequencing.

In some embodiments, nucleotide sequencing comprises template-dependent replication of the DNA region that results in incorporation of labeled nucleotides (e.g., fluorescently labeled nucleotides), and wherein an arrival time and/or duration of an interval between signal generated from different incorporated nucleotides is determinative of the presence or absence of the modification and/or the identity of an incorporated nucleotide.

Single-Molecule, Real-Time Sequencing

In some embodiments, genomic DNA comprising a target DNA region is sequenced by single-molecule, real-time (SMRT) sequencing. SMRT sequencing is a process by which single DNA polymerase molecules are observed in real time while they catalyze the incorporation of fluorescently labeled nucleotides complementary to a template nucleic acid strand. Methods of SMRT sequencing are known in the art and were initially described by Flusberg et al., *Nature Methods,* 7:461-465 (2010), which is incorporated herein by reference for all purposes.

Briefly, in SMRT sequencing, incorporation of a nucleotide is detected as a pulse of fluorescence whose color identifies that nucleotide. The pulse ends when the fluorophore, which is linked to the nucleotide's terminal phosphate, is cleaved by the polymerase before the polymerase translocates to the next base in the DNA template. Fluorescence pulses are characterized by emission spectra as well as by the duration of the pulse ("pulse width") and the interval between successive pulses ("interpulse duration" or "IPD"). Pulse width is a function of all kinetic steps after nucleotide binding and up to fluorophore release, and IPD is a function of the kinetics of nucleotide binding and polymerase translocation. Thus, DNA polymerase kinetics can be monitored by measuring the fluorescence pulses in SMRT sequencing.

In addition to measuring differences in fluorescence pulse characteristics for each fluorescently-labeled nucleotide (i.e., adenine, guanine, thymine, and cytosine), differences can also be measured for non-methylated versus methylated bases. For example, the presence of a methylated base alters the IPD of the methylated base as compared to its non-methylated counterpart (e.g., methylated adenosine as compared to non-methylated adenosine). Additionally, the presence of a methylated base alters the pulse width of the methylated base as compared to its non-methylated counterpart (e.g., methylated cytosine as compared to non-methylated cytosine) and furthermore, different modifications have different pulse widths (e.g., 5-hydroxymethylcytosine has a more pronounced excursion than 5-methylcytosine). Thus, each type of non-modified base and modified base has a unique signature based on its combination of IPD and pulse width in a given context. The sensitivity of SMRT sequencing can be further enhanced by optimizing solution conditions, polymerase mutations and algorithmic approaches that take advantage of the nucleotides' kinetic signatures, and deconvolution techiques to help resolve neighboring methylcytosine bases.

Nanopore Sequencing

In some embodiments, nucleotide sequencing does not comprise template-dependent replication of a DNA region. In some embodiments, genomic DNA comprising a target DNA region is sequenced by nanopore sequencing. Nanopore sequencing is a process by which a polynucleotide or nucleic acid fragment is passed through a pore (such as a protein pore) under an applied potential while recording modulations of the ionic current passing through the pore. Methods of nanopore sequencing are known in the art; see, e.g., Clarke et al., *Nature Nanotechnology* 4:265-270 (2009), which is incorporated herein by reference for all purposes.

Briefly, in nanopore sequencing, as a single-stranded DNA molecule passes through a protein pore, each base is registered, in sequence, by a characteristic decrease in current amplitude which results from the extent to which each base blocks the pore. An individual nucleobase can be identified on a static strand, and by sufficiently slowing the rate of speed of the DNA translocation (e.g., through the use of enzymes) or improving the rate of DNA capture by the pore (e.g., by mutating key residues within the protein pore), an individual nucleobase can also be identified while moving.

In some embodiments, nanopore sequencing comprises the use of an exonuclease to liberate individual nucleotides from a strand of DNA, wherein the bases are identified in order of release, and the use of an adaptor molecule that is covalently attached to the pore in order to permit continuous base detection as the DNA molecule moves through the pore. As the nucleotide passes through the pore, it is characterized by a signature residual current and a signature dwell time within the adapter, making it possible to discriminate between non-methylated nucleotides. Additionally, different dwell times are seen between methylated nucleotides and the corresponding non-methylated nucleotides (e.g., 5-methyl-dCMP has a longer dwell time than dCMP), thus making it possible to simultaneously determine nucleotide sequence and whether sequenced nucleotides are modified. The sensitivity of nanopore sequencing can be further enhanced by optimizing salt concentrations, adjusting the applied potential, pH, and temperature, or mutating the exonuclease to vary its rate of processivity.

In some embodiments, the DNA is hybridized to another nucleic acid. In some embodiments, the nucleic acid is linked to a solid support. For example, in some embodiments, the DNA is hybridized to a microarray. A microarray is useful, for example, in monitoring the presence, absensce or quantity of multiple sequences in the DNA. In some embodiments, DNA from different samples can be hybridized to one or more nucleic acids, thereby determining the differential amount of one or more particular sequence between the samples, Thus, for example, diseased and healthy cells, or cells obtained at different times, or before and after or during treatment can be compared.

The present methods can include correlating accessibility of a DNA region to transcription from that same region. In some embodiments, experiments are performed to determine a correlation between accessibility and gene expression and subsequently accessibility of a DNA modifying agent to a particular DNA region can be used to predict transcription from the DNA region. In some embodiments, transcription from a DNA region and accessibility of that region to DNA modifying agents are both determined. A wide variety of methods for measuring transcription are known and include but are not limited to, the use of northern blots and RT-PCR.

In some embodiments, the DNA methylation status of a region can be correlated with accessibility of a DNA region to the DNA modifying agent. In some embodiments, experiments are performed to determine a correlation between accessibility and DNA methylation in the region and subsequently accessibility of a DNA modifying agent to a particular DNA region can be used to predict DNA methylation from the DNA region. In some embodiments, methylation of a DNA region and accessibility of that region to DNA modifying agents are both determined. A wide variety of methods for measuring DNA methylation are known and include but are not limited to, the use of bisulfite (e.g., in sequencing and/or in combination with methylation-sensitive restriction enzymes (see, e.g., Eads et al., *Nucleic Acids Research* 28(8): E32 (2002)) and the high resolution melt assay (HRM) (see, e.g., Wodjacz et al, *Nucleic Acids Research* 35(6):e41 (2007)).

In some embodiments, comparisons of the presence, absence, or quantity of a first DNA region in the diffused smaller DNA fragments and/or in the non-diffused larger DNA is compared with the presence, absence, or quantity of a second DNA region from the same cell(s). In some embodiments, the second DNA region is a control region, e.g., a DNA region that is known to be accessible or inaccessible. Alternatively, or in addition, one can compare presence, absence, or quantity of a first DNA region in the diffused smaller DNA fragments and/or in the non-diffused larger DNA in two different cells. For example, the two cells can represent diseased and healthy cells or tissues, different cell types, different stages of development (including but not limited to stem cells or progenitor cells), cells obtained at different times from an individual, etc. Thus, by using the methods of the invention one can detect differences in chromatin structure between cells and/or determine relative chromatin structures between two or more DNA regions (e.g., genes) within one cell. In addition, one can determine the effect of a drug, chemical or environmental stimulus on the chromatin structure of a particular region in the same cells or in different cells.

Protein Analysis

As noted above, in addition to DNA analysis, protein associated with the diffused DNA can also be analyzed. The protein can be analyzed as desired. In some embodiments, the protein(s) is microsequenced to determine its amino acid sequence. In some embodiments, the protein is analyzed with one or more immunuological method. For example, an antibody of known specificity can be contacted to the protein to determine whether the protein binds the antibody, thereby suggesting the protein's identity.

VIII. Samples

A variety of eukaryotic cells can be used in the present invention. In some embodiments, the cells are animal cells, including but not limited to, human, or non-human, mammalian cells. Non-human mammalian cells include but are not limited to, primate cells, mouse cells, rat cells, porcine cells, and bovine cells. In some embodiments, the cells are non-mammalian cells, e.g., avian, reptilian, or other cells. In some embodiments, the cells are plant cells. Cells can be, for example, cultured primary cells, immortalized culture cells or can be from a biopsy or tissue sample, optionally cultured and stimulated to divide before assayed. Cultured cells can be in suspension or adherent prior to and/or during the permeabilization and/or DNA modification steps. In some embodiments, the cells can be from a tumor biopsy.

IX. Diagnostic and Prognostic Methods

The present invention also provides methods for diagnosing or providing a prognosis for a disease or condition or determining a course of treatment for a disease or condition based on the accessibility or inaccessibility of DNA regions in genomic DNA.

In some embodiments, accessibility of a DNA region of interest to a DNA cleaving agent is increased (or at least is present) or decreased (or absent) in a diseased cell or tissue as compared to a normal (i.e., non-diseased) cell or tissue. In these embodiments, detection of the presence or absence or quantity of copies of the DNA region of interest can be used as a diagnostic or prognostic tool.

Once a diagnosis or prognosis is established using the methods of the invention, a regimen of treatment can be established or an existing regimen of treatment can be altered in view of the diagnosis or prognosis. For instance, detection of a cancer cell according to the methods of the invention can lead to the administration of chemotherapeutic agents and/or radiation to an individual from whom the cancer cell was detected.

A variety of DNA regions can be detected either for research purposes and/or as a control DNA region to confirm that the reagents were performing as expected. For example, in some embodiments, a DNA region is assayed that is known to be accessible or inaccessible. Such DNA regions are useful, for example, as positive or negative controls for accessibility.

X. Kits

The present invention also provides kits for performing the methods described herein. A kit can optionally include written instructions or electronic instructions (e.g., on a CD-ROM or DVD). Kits of the present invention can include, e.g., a DNA modifying agent and/or a DNA cleaving agent; a cell permeabilization agent; and an affinity agent that specifically binds to a DNA-binding protein. The DNA cleaving agent can comprise, for example, a DNase or a restriction enzyme or a DNA cleaving polypeptide fused to a heterologous DNA-recognition polypeptide. The DNA modifying agent can be, for example, a DNA methyltransferase. The permeabilization agent can be, for example, a lysolipid or a nonionic detergent. The affinity agent can, for example, specifically bind to a histone, a modified histone, an RNA polymerase, a transcription factor, a TATA box-binding protein (TBP), or other DNA-binding protein and can be, e.g., an antibody. In some cases, the affinity agent is linked to a solid support. Exemplary solid supports include, e.g., a bead or particle. In some embodiments, the bead or particle is magnetic or attracted to magnets.

The kits of the invention can also include one or more control cells and/or nucleic acids. Exemplary control nucleic acids include, e.g., those comprising a gene sequence that is either accessible in essentially all cells of an animal (e.g., a housekeeping gene sequence or promoter thereof) or inaccessible in most cells of an animal. In some embodiments, the kits include one or more sets of primers for amplifying such gene sequences (whether or not the actually gene sequences or cells are included in the kits). For example, in some embodiments, the kits include a DNA modifying agent, a DNA cleaving agent, and a cell permeabilizing and/or cell disrupting agent, an affinity agent that specifically binds to a DNA-binding protein, and one or more primer sets for amplifying a control DNA region (including but not limited to a control gene as described herein), and optionally one or more primer sets for amplifying a second DNA region, e.g., a target DNA region.

EXAMPLES

Example 1

This example demonstrates that small DNA fragments can be obtained from permeabilized Hela cells following introduction of DNase I into the cells. Hela cells were grown in a standard 6-well tissue culture plate to 95% confluence, about 1 million cells per well. The culture media was aspirated and 500 µl of a permeabilization/digestion buffer was gently layered on the cells. The permeabilization/digestion buffer consisted of lysolecithin, Tris-HCl, $MgCl_2$, $CaCl_2$ and DNase I. The permeabilized cells were then incubated at 37° C. for 30 minutes. Following incubation the permeabilization/digestion buffer was collected in a 1.5 ml eppendorf tube and placed on ice for 2 minutes. The sample was then centrifuged in a microcentrifuge at 13,000 rpm for 2 minutes and the supernatent was transfered to a new 1.5 ml eppendorf tube. The sample was then re-centrifuged at 13,000 rpm for 5 min and 400 µl of the supernatant was transfered to a new 1.5 ml eppendorf tube. 100 ul of lysis/stop buffer was then added to the sample; the sample was mixed and incubated at 37° C. for 10 minutes. The lysis/stop buffer consisted of Tris-HCl, NaCl, EDTA, N-laurolysarcosine, RNase A and proteinase K. The DNA was then isolated using a commercial nucleic acid purification kit (Aurum, Bio-Rad) following standard procedures. 1 ul of each sample was then analyzed using the high sensitivity chip in the BioAnalyzer (Agilent). 10 ul each sample was diluted to 50 ul and analyzed by qPCR on a Bio-Rad CFX 384-well real time PCR instrument using RHO and GAPDH primer sets and the following protocol: 96° C. for 5 minutes followed by 40 cycles of 96° C. for 30 seconds/66° C. for 1 minute.

Figure 5:
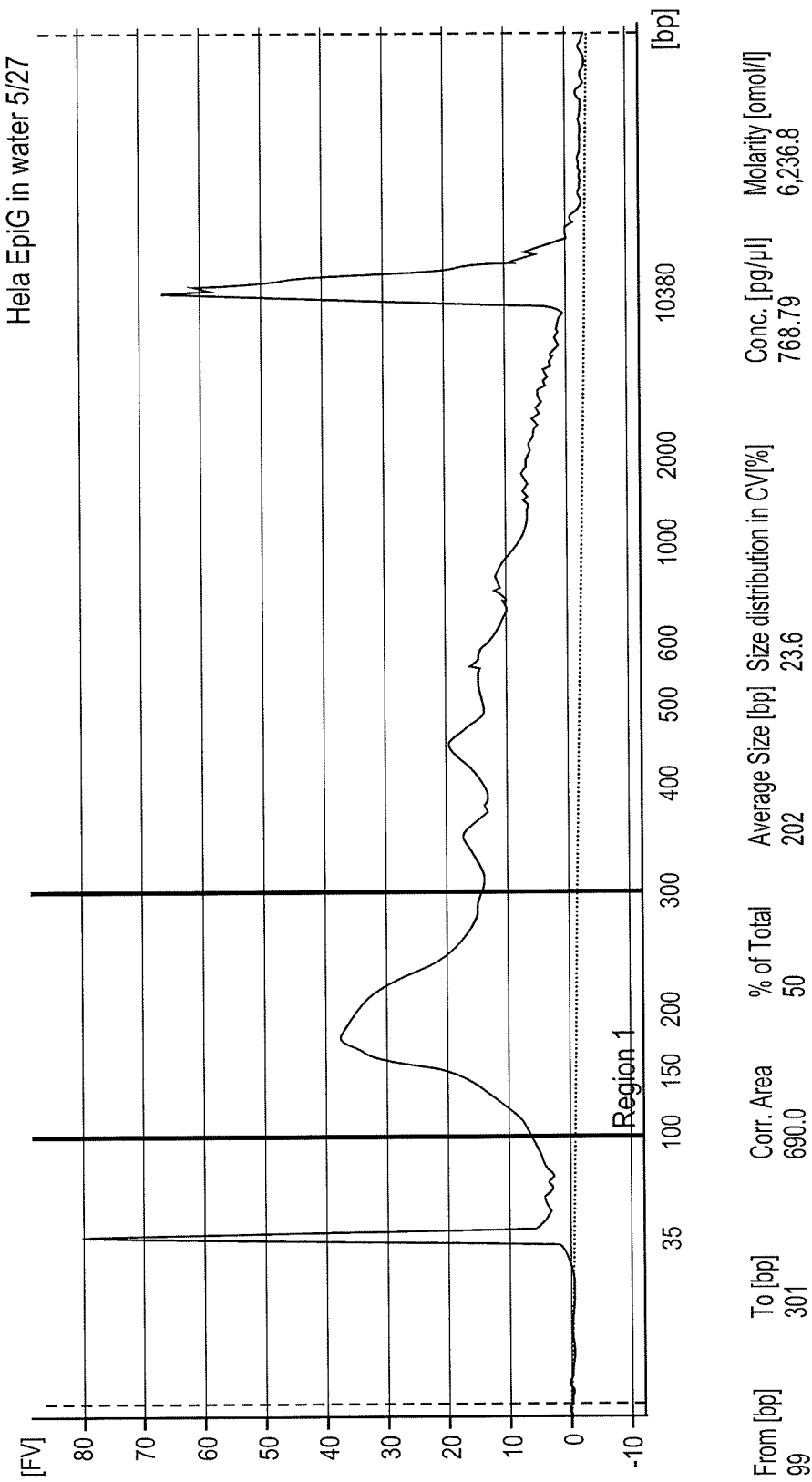
FIG. 5 illustrates a BioAnalyzer tracing of the supernatant of Hela cells that were permeabilized and treated with DNase I. A peak was observed in the 100-300 bp range, though some DNA was present over 2 kb. In contrast, DNA isolated from the cell would be much larger (over 10,000 bp). This indicates that the DNA that diffused from the permeabilized cells is indeed smaller than the bulk of DNA in the cell and that the permeabilized cell is acting like a size filter for DNA. The sharp peaks at the low and high molecular weight ranges are size standards.

FIG. 5 illustrates a BioAnalyzer tracing of the supernatant of Hela cells that were permeabilized and treated with DNase I. A peak was observed in the 100-300 bp range, though some DNA was present over 2 kb. In contrast, DNA isolated from the cell would be much larger (over 10,000 bp). This indicates that the DNA in the supernatant is indeed smaller than the bulk of DNA in the cell and that the permeabilized cell is acting like a size filter for DNA.

Figure 6:
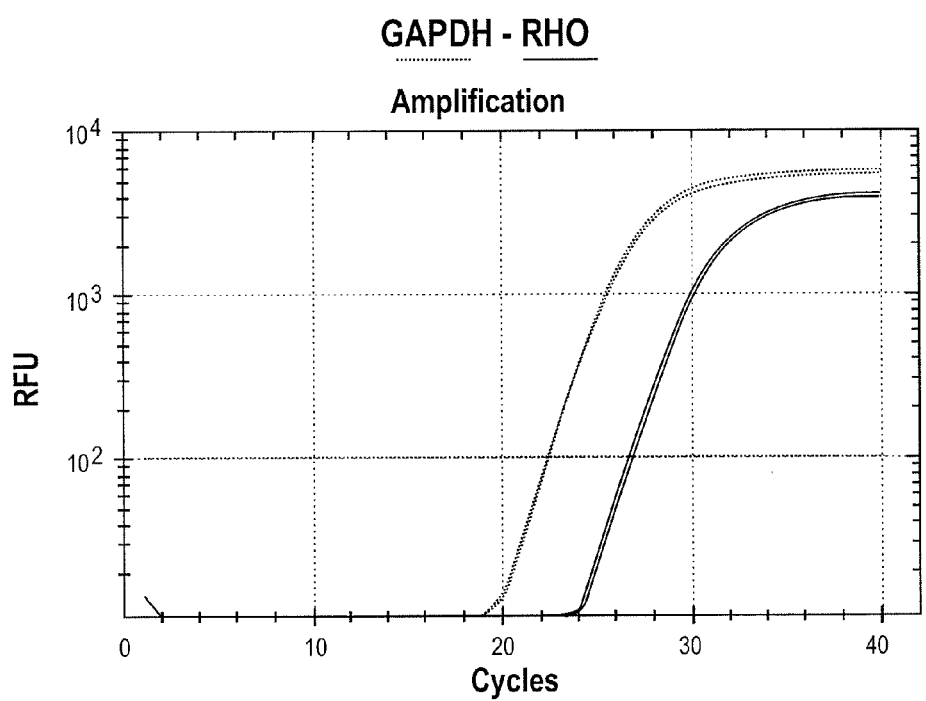
FIG. 6 illustrates qPCR analysis of the Hela sample (permeabilized and DNase I-treated). The GAPDH and RHO promoters were amplified. The GAPDH promoter (left amplification curve), which is in accessible chromatin, is highly enriched relative to the RHO promoter (right amplification curve), which is in inaccessible chromatin. This indicates that accessible chromatin is enriched in the supernatant from permeabilized and DNase I-treated cells.

DNA in the supernatant was also analyzed by qPCR. Specifically, GAPDH and RHO promoters were amplified using the following protocol: 96° C. for 5 minutes followed by 40 cycles of 96° C. for 30 seconds/66° C. for 1 minute. As illustrated in FIG. 6, the GAPDH promoter (left amplification curve), which is in accessible chromatin, was highly enriched relative to the RHO promoter (right amplification curve), which is in inaccessible chromatin. This indicated that accessible chromatin is enriched in the supernatant from permeabilized and DNaseI-treated cells.

Figure 7:
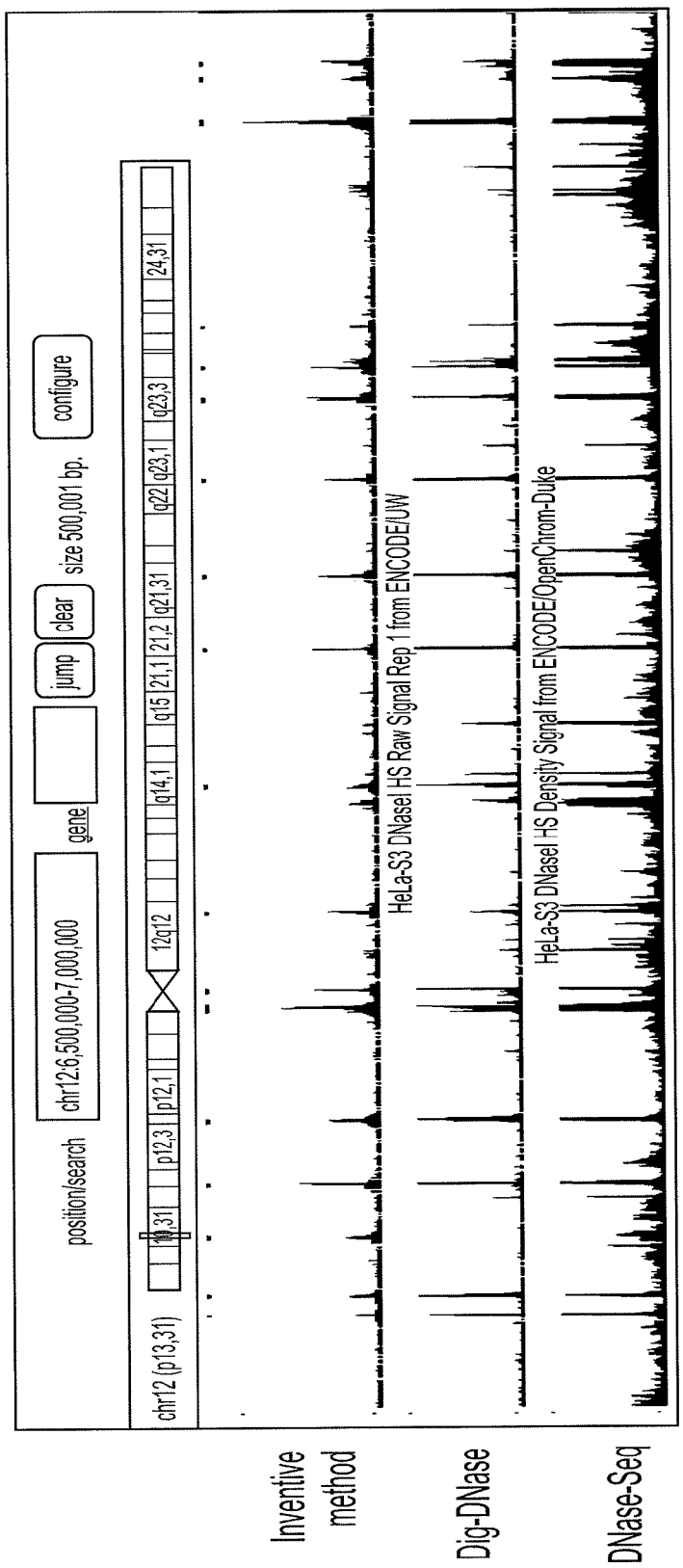
FIG. 7 provides next-generation sequencing data for DNA from the supernatant of permeabilized and DNase I-treated Hela cells. The data is presented to show regions within the genome where the supernatant DNA was observed ("Inventive method" lane on the UCSC genome browser). The data was compared to publicly available data that maps accessible chromatin regions on a genome-wide scale using other techniques (Digital DNase and DNase-Seq lanes). The peaks for the supernatant DNA correlate well with the peaks using the other techniques. This demonstrates that method described herein maps accessible chromatin regions as well as other current, well characterized techniques. Notably, the method described herein is faster and requires less starting material than the other techniques, in addition, it does not require nuclei isolation which is a requirement of the other techniques.

DNA in the supernatant of the permeabilized and DNase I-treated Hela cells was also sequenced on an Illumina Genome Analyzer II using a 36 cycle single-end sequencing protocol. FIG. 7 provides a summary of sequencing results of DNA from the supernatant. FIG. 7 shows regions within the genome where the supernatant DNA was observed ("Inventive method" lane on the UCSC genome browser). The data was compared to publicly available data that maps accessible chromatin regions on a genome-wide scale using other techniques (Digital DNase and DNase-Seq lanes). The peaks for the supernatant DNA correlate well with the peaks using the other techniques. This demonstrates that method described herein maps accessible chromatin regions as well as the other current, well characterized techniques. Notably, the method described herein is faster, requires less starting material, and does not require nuclei isolation.

Example 2

This example demonstrates that small DNA fragments can be obtained from permeabilized cells from tissue samples following introduction of DNase I into the cells.

Figure 9A:
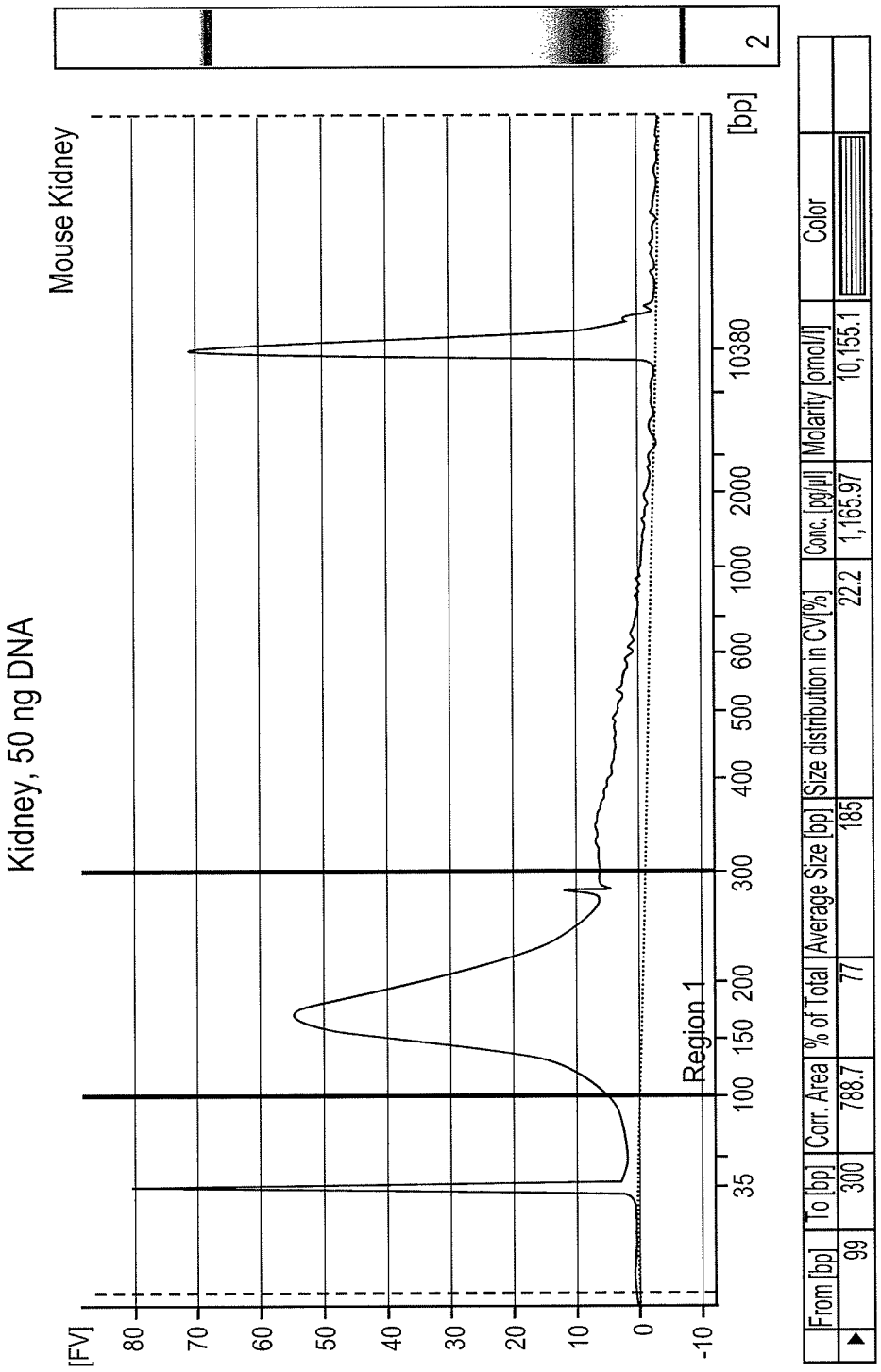
FIGS. 9A and 9B provide an exemplary BioAnalyzer tracing of mouse tissue—kidney (9A) and brain (9B)—supernatant samples generated according to the method described herein. This indicates that tissue samples, as well as cells, can be used as starting material for the methods described herein.
Figure 9B:
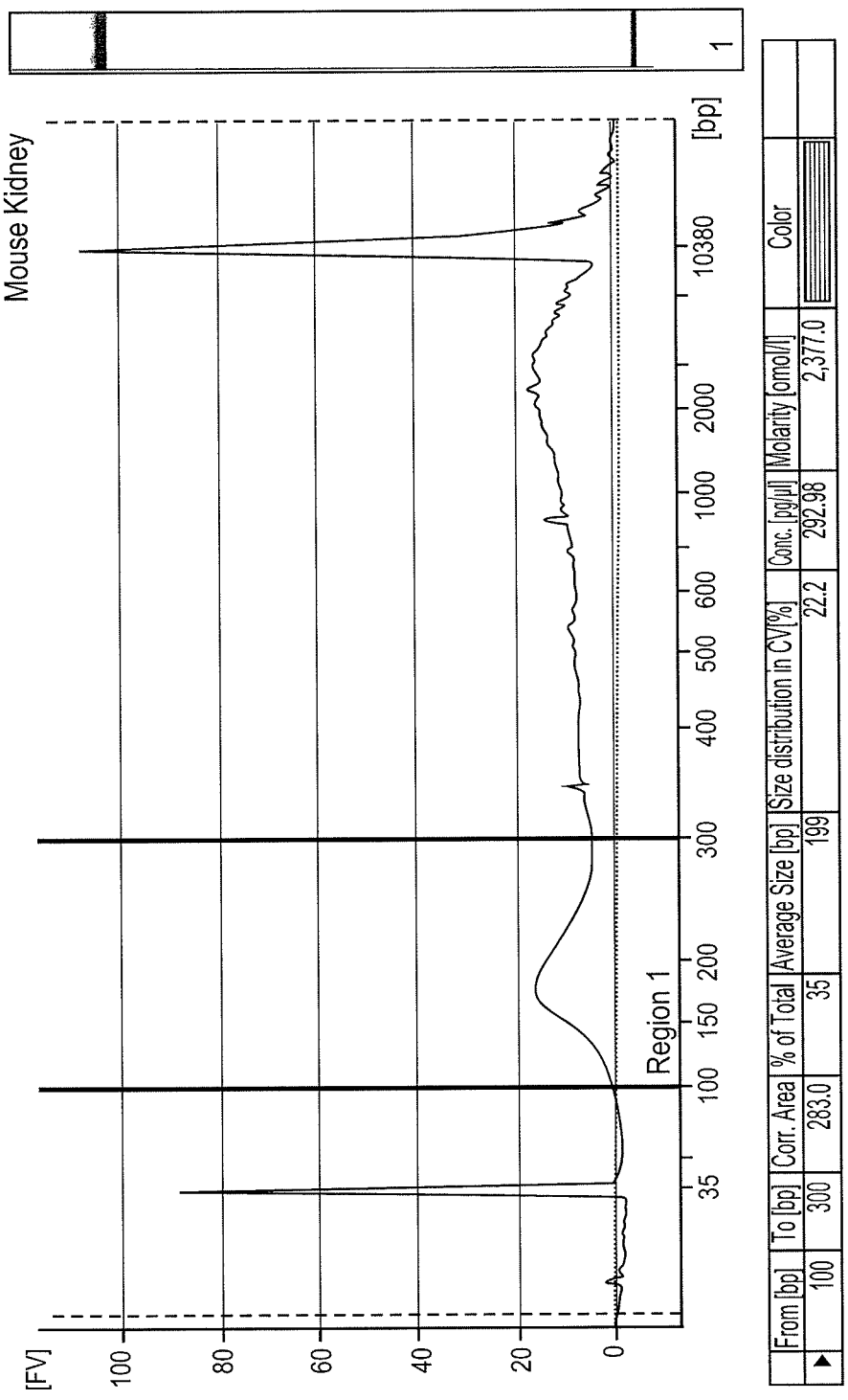

FIGS. 9A and 9B provide an exemplary BioAnalyzer tracing of mouse tissue—kidney (9A) and brain (9B)—supernatant samples generated according to the method described herein. This indicates that tissue samples, as well as cells, can be used as starting material.

Figure 10:
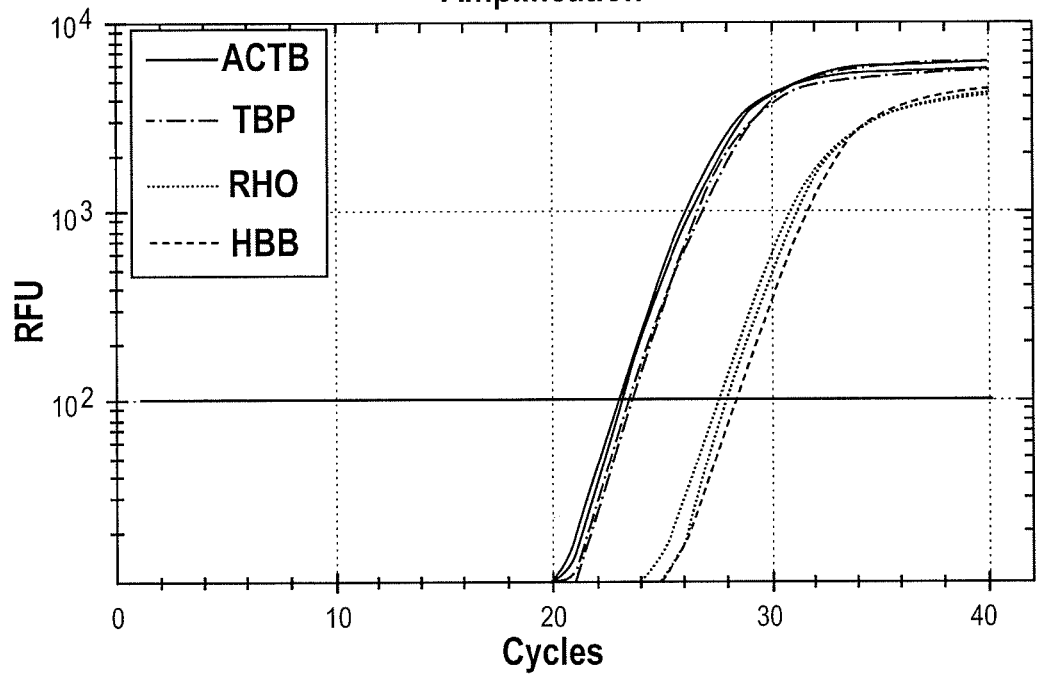
FIG. 10 provides a qPCR analysis of the mouse tissue samples discussed in FIGS. 9A-B. In this qPCR analysis, the ACTB and TBP promoters, which are known from other data to be in accessible chromatin, and the RHO and HBB promoters, which are in inaccessible chromatin, were amplified. The ACTB and TBP promoters were highly enriched relative to the RHO and HBB promoters. This indicates that, as expected, accessible chromatin is enriched in the tissue samples and shows that the procedure is useful for tissue and biopsy samples.
Figure 10:
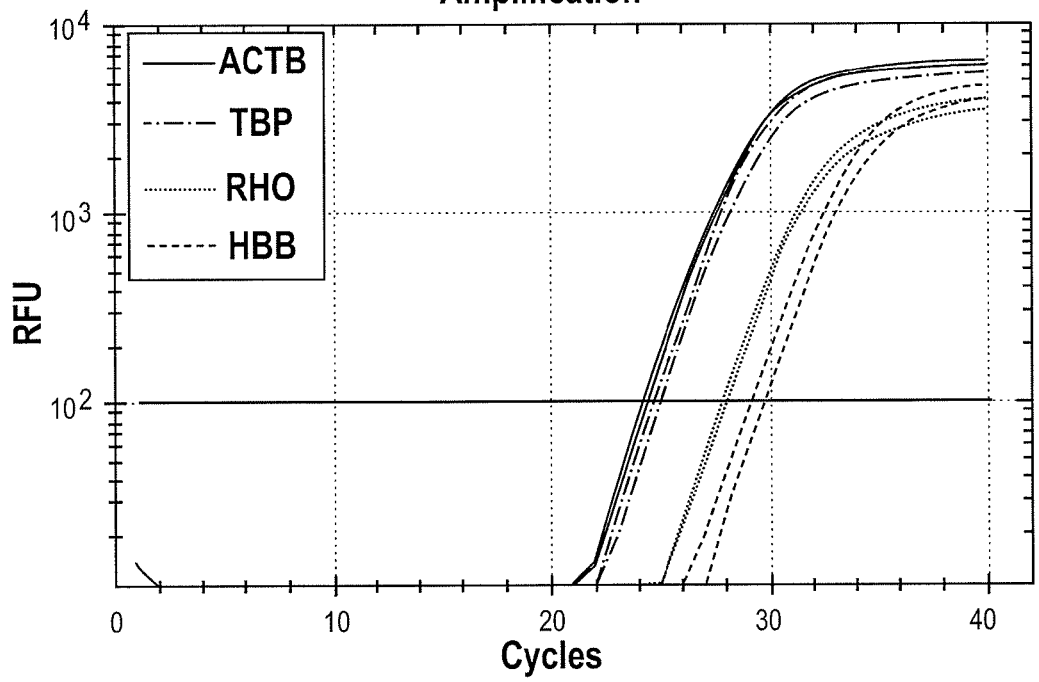

Similar to Example 1, supernatant DNA from the tissue was submitted to quantitative PCR. In this case, two promoters known to be accessible (the ACTB and TBP promoters), and two promoters known to be inaccessible (the RHO and HBB promoters), were amplified. See, FIG. 10. The ACTB and TBP promoters were highly enriched relative to the RHO and HBB promoters. This indicates that, as expected, accessible chromatin is enriched in the tissue samples and shows that the procedure will work in tissue and biopsy samples.

Example 3

This example demonstrates that DNA binding proteins associated with genomic DNA can be obtained from permeabilized cells. The example also demonstrates that DNA complexed with DNA-binding proteins can be enriched (and subsequently analyzed) using an agent that specifically binds the target DNA-binding protein.

Chromatin immunoprecipitation (ChIP) is a powerful tool that identifies DNA regions associated with specific proteins, transcription factors, or histone variants. It can be used to map transcription regulation and control elements genome-wide. As explained above, a novel technology for isolating active chromatin was been developed. When permeabilized cells are treated with a nuclease, small DNA fragments, corresponding to active chromatin, diffuses out of cell and can be collected. These small DNA fragments, when analyzed, for example, by next-generation sequencing, provide a global map of active chromatin regions.

We show in this example that the active chromatin that has diffused from the cell is still associated with its cognate DNA-binding proteins and histones. Based on this finding, a novel ChIP method that does not require protein-DNA cross-linking or DNA shearing is provided. Using this method (1) RNA polymerase II (RNAPII), (2) TBP and (3) histone H3 trimethylated on lysine 4 (H3K4me3) were each demonstrated to be associated with active promoters, but rarely detected at silenced promoters. Comparison of the ChIP method described herein with a standard ChIP assay shows that immunoprecipitation (IP) efficiency is similar, but IP specificity is dramatically different. To measure IP specificity, the ratio of active promoter DNA precipitated with RNAPII (signal) was compared relative to inactive promoter DNA precipitated (noise). We find that the new ChIP method described here yields highly specific IP with a signal-to-noise ratio of >300; however standard ChIP is much less specific with a signal-to-noise ratio of about 6. We conclude that the new ChIP method described here offers two significant advantages over standard ChIP: dramatically reduced background and a much easier workflow.

Figure 3:
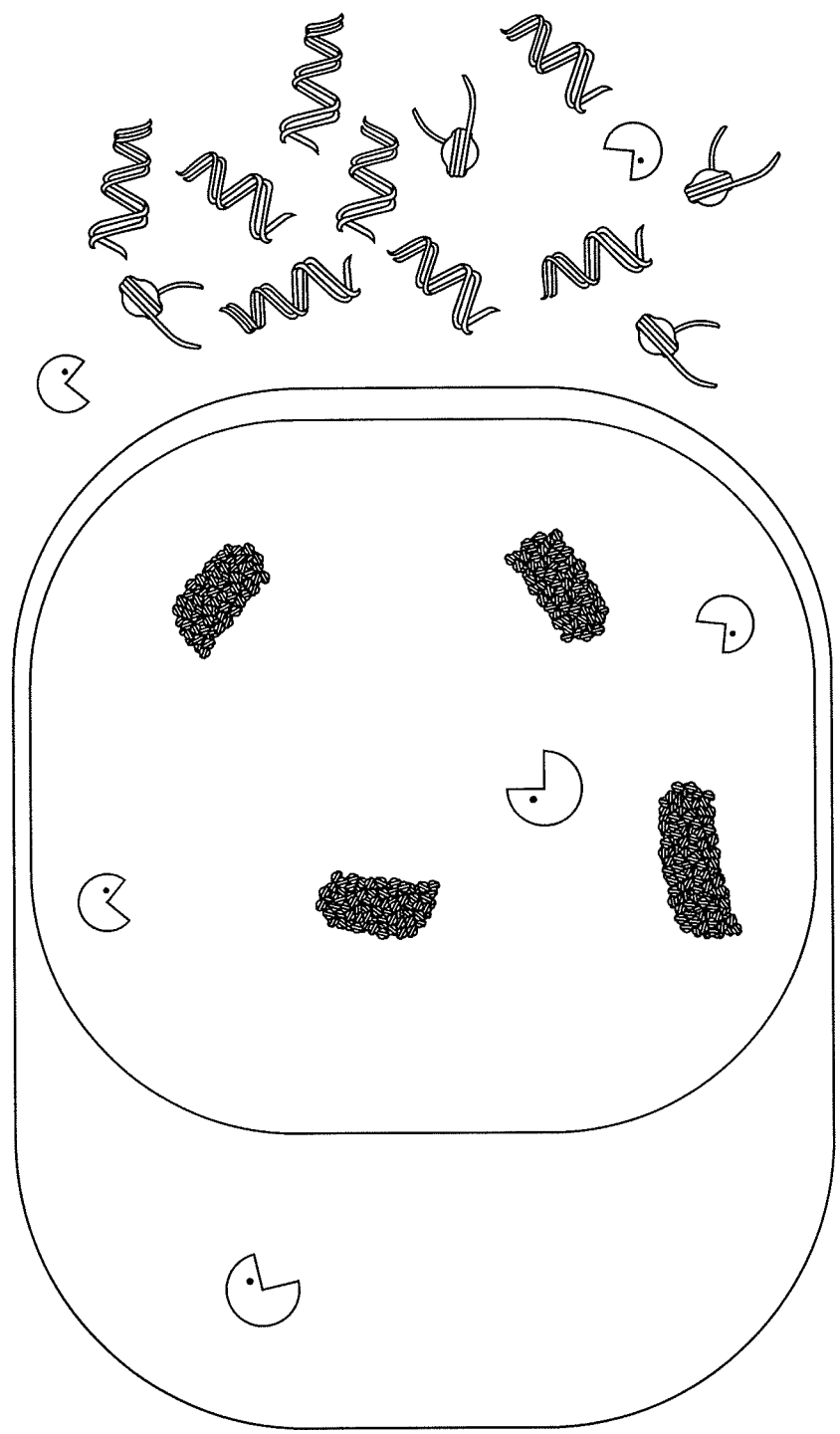
FIG. 3 schematically represents a discovery provided herein, namely that the permeabilized cells allow small DNA fragments or protein-DNA complexes, corresponding to accessible chromatin, to diffuse out of the cell. The inaccessible chromatin is not digested and cannot diffuse out of the cell because it is too large to efficiently pass through the permeabilized cell membrane.

As depicted in FIG. 3, DNA fragments from active chromatin diffuse out of cells after nuclease treatment. Proteins that bind to their target DNA sites will also diffuse out of the cell and into the supernatant. When physiological cell conditions are provided, these proteins will maintain binding status to their DNA target sites. To verify that proteins are still bound to their target sites from diffused DNA fragments we choose RNAPII, TATA box binding protein (TBP) and H3K4m3, three proteins known to bind to active promoters but not inactive promoters.

Figure 11:
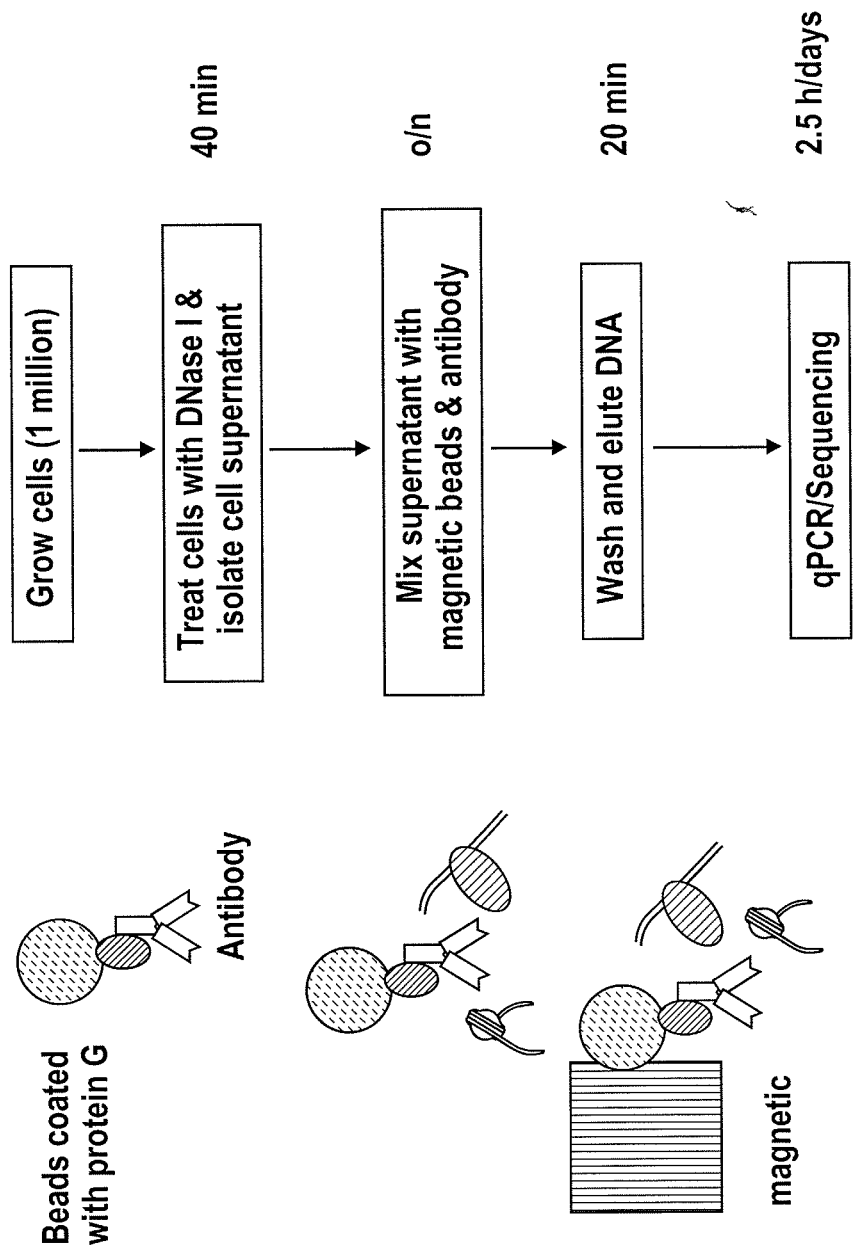
FIG. 11 provides a summary of a method for detection of proteins associated with diffused DNA.

Our general approach is depicted in FIG. 11. Briefly, Hela cells were grown and treated with DNase I as described above and subsequently centrifuged and the supernatant was removed. The supernatant was incubated with antibodies specific for RNAII, TBP or H3K4m3 linked to magnetic beads via protein G, centrifuged, and the supernatant was removed. The beads were washed and subsequently eluted by incubating the beads with 500 µl of 1 mM TRIS-HCl, pH 8.5 and incubated at 95° C. for 5 minutes. qPCR analyses were performed using primers that amplify promoter regions from active or silenced genes to detect DNA in the eluate.

Figure 12:
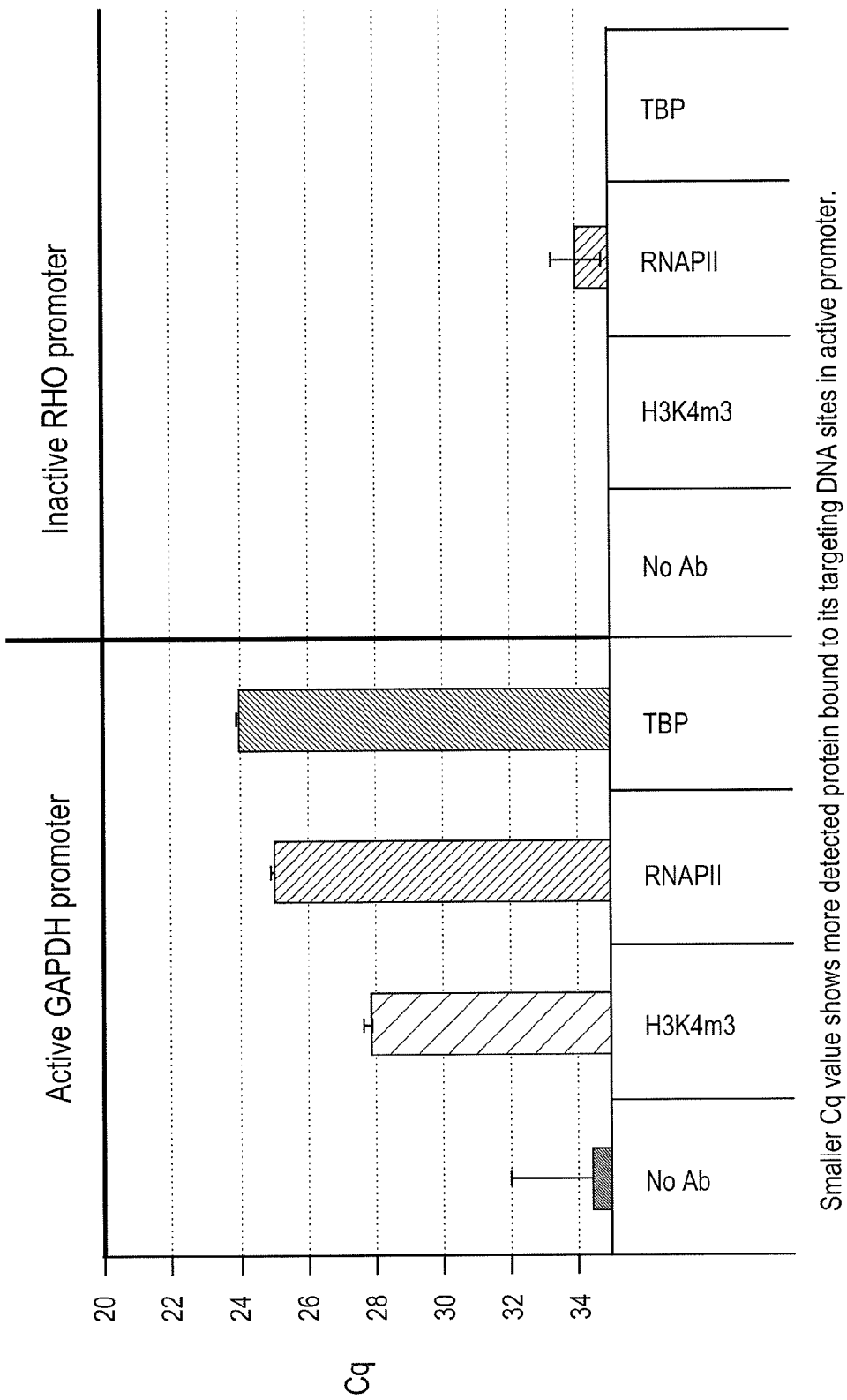
FIG. 12 shows that qPCR detects DNA bound to target proteins in active promoter regions, but not inactive promoter regions.

The results (see FIG. 12) show that qPCR detected protein bound to DNA in the active (GAPDH) promoter region for all three proteins, but detected little protein bound to DNA in the inactive (RHO) promoter region.

Figure 13:
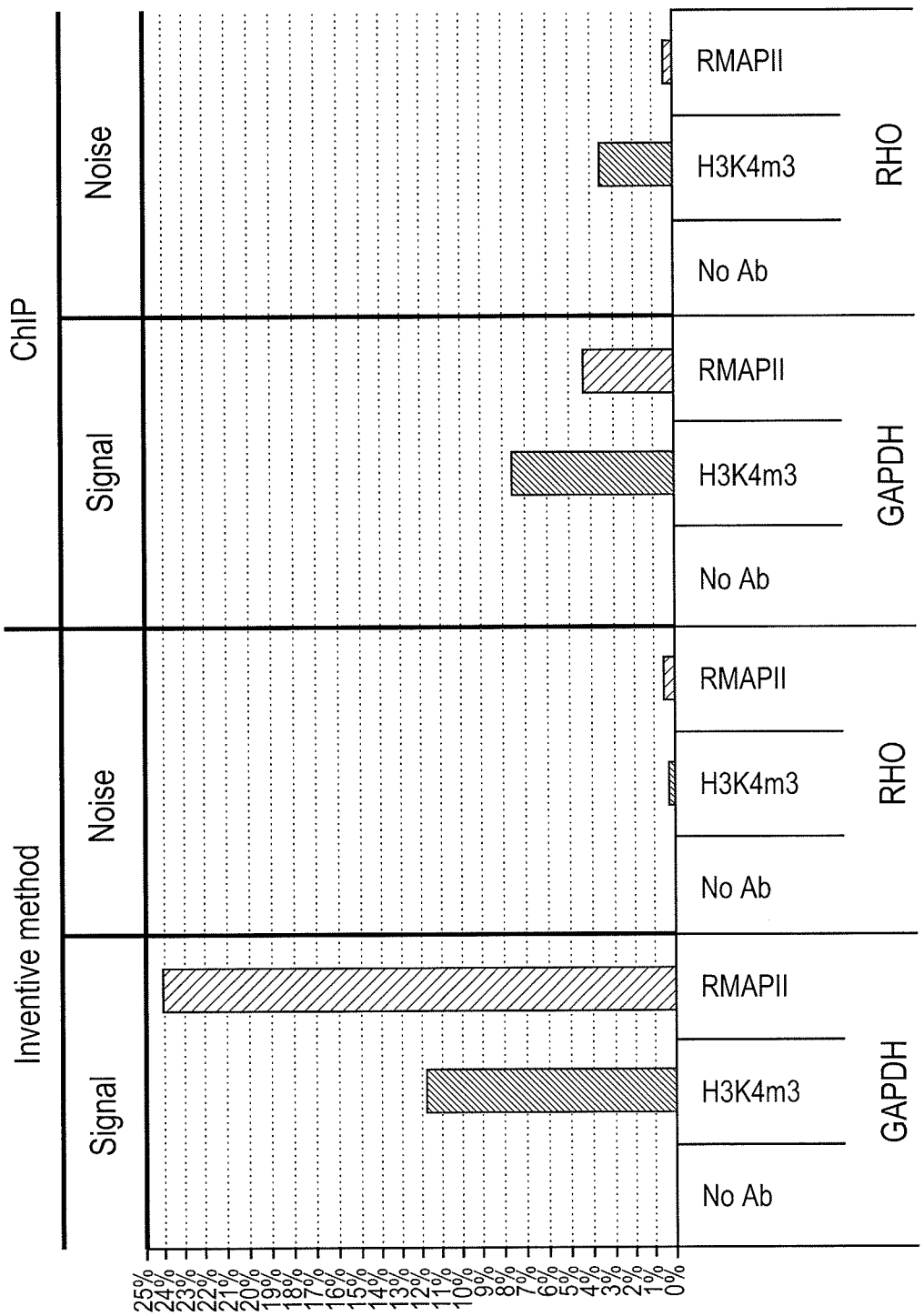
FIG. 13 shows that the method depicted in FIG. 11 is more efficient than standard ChIP for detection of protein-associated active promoters

We also compared our data with standard ChIP technology and showed that the inventive assay depicted in FIG. 11 has similar or better detection efficiency than standard ChIP technology. See, FIG. 13.

Figure 14:
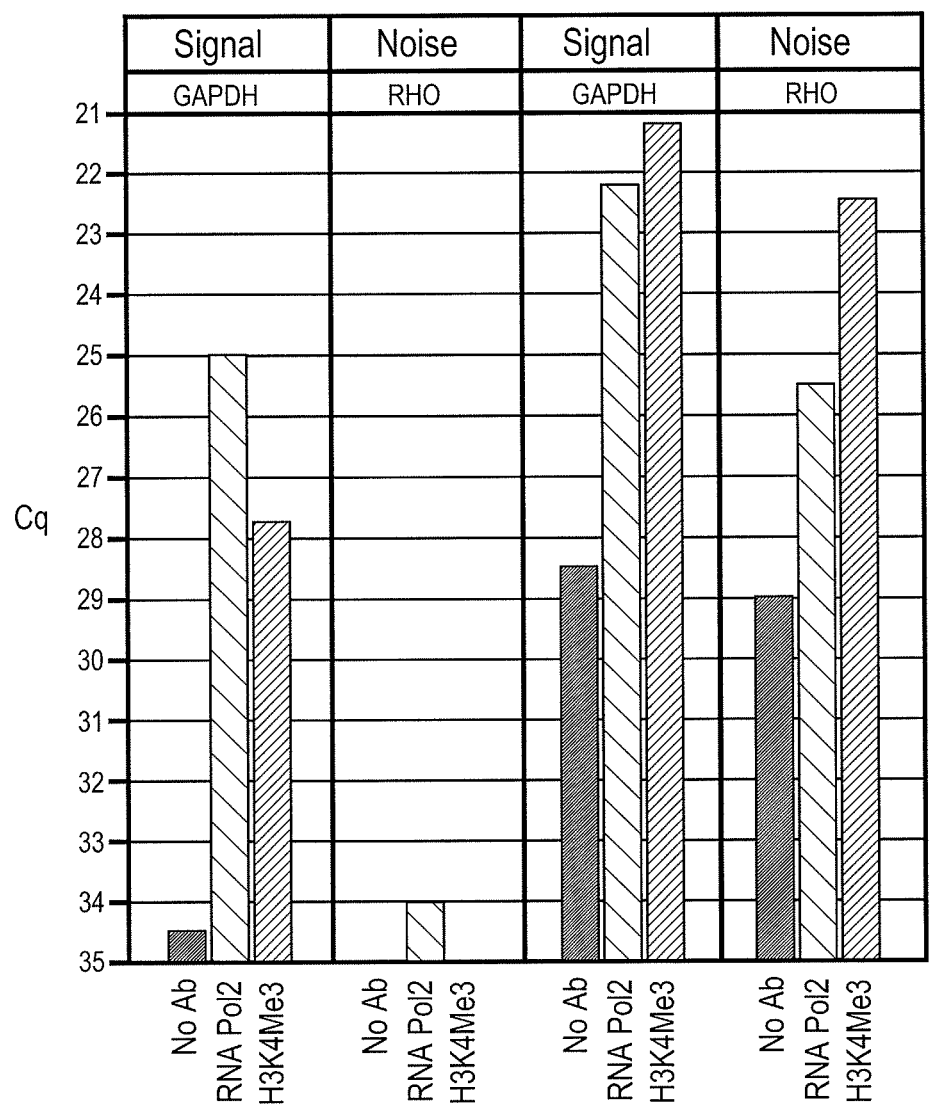
FIG. 14 shows that the method (left two columns) depicted in FIG. 11 has a higher signal-to-noise ratio than standard ChIP (right two columns).

Further, we used qPCR-detected RNAPII bound DNA from active promoter GAPDH as signal and from inactive promoter RHO as noise to determine our method's and standard ChIP's specificity. The results (FIG. 14) show our method has a dramatic signal-to-noise ratio than standard ChIP.

To generate additional data we performed next-generation sequencing of the samples that were analyzed by qPCR. The sequencing was performed on an Illumina Genome Analyzer IIx using a 36 base, single-end read protocol. The reads were mapped to the human genome (hg19) and a bigWig file indicating tag-count was generated. The data from the bigWig files was mapped back to the human genome and visualized on the UCSC genome browser. We found that our method was better at detecting biologically relevant protein-DNA interactions than traditional ChIP analyses performed by the ENCODE consortium and publically available on the UCSC Genome Browser (data not shown).

We developed a novel method for identifying protein binding sites in the genome. This new ChIP assay does not require DNA-protein cross linking and DNA shearing. It makes running a ChIP assay much easier. Our method detects proteins bound to active DNA regions in the genome. It dramatically reduces assay background. Comparing with standard ChIP assay our assay is more specific for its targets, having a dramatic higher signal-to-noise ratio than standard ChIP. This will provide, for example, more accurate genome-wide mapping of gene regulation network.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of separating DNA accessible to a DNA cleaving agent in a permeabilized cell from DNA inaccessible to the DNA cleaving agent, the method comprising:
   a) permeabilizing a cell having genomic DNA, thereby generating a permeabilized cell; introducing a DNA cleaving agent into the permeabilized cell having genomic DNA under conditions such that the DNA cleaving agent cleaves the genomic DNA in the cell, thereby generating cleaved DNA;
   b) separating cleaved DNA that diffuses out of the intact permeabilized cell from the cell; and
   c) introducing a DNA modifying agent into the permeabilized cell such that the DNA modifying agent modifies the genomic DNA in the cell, wherein the DNA modifying agent is a DNA methyltransferase.

2. The method of claim 1, wherein the DNA modifying agent and the DNA cleaving agent are introduced simultaneously or the DNA modifying agent is introduced before the DNA cleaving agent is introduced.

3. The method of claim 1, wherein the DNA cleaving agent is DNase I or micrococcal nuclease.

4. The method of claim 2, wherein the DNA modifying agent adds modifications to at least some recognition sequences of the DNA cleaving agent, and the DNA cleaving agent does not cleave recognition sequences with the modification.

5. The method of claim 2, wherein the DNA modifying agent adds modifications to at least some recognition sequences of the DNA cleaving agent, and the DNA cleaving agent cleaves recognition sequences with the modification and does not cleave recognition sequences lacking the modification.

6. The method of claim 1, wherein the DNA modifying agent is introduced after the DNA cleaving agent is introduced.

7. The method of claim 1, wherein the permeabilizing and the introducing occur simultaneously.

8. The method of claim 1, further comprising isolating the cleaved DNA.

9. The method of claim 1, further comprising isolating DNA remaining in the intact cell following the separating.

10. The method of claim 1, wherein the DNA cleaving agent comprises a DNA cleaving polypeptide fused to a heterologous DNA-recognition polypeptide.

11. The method of claim 8, wherein the isolating comprises affinity purifying the DNA.

12. The method of claim 1, further comprising analyzing the separated DNA.

13. The method of claim 12, wherein the analyzing comprises nucleotide sequencing the separated DNA.

14. The method of claim 12, wherein the analyzing comprises an amplification reaction.

15. The method of claim 12, wherein two or more nucleic acids are associated with one or more proteins and the analyzing comprises ligating the two or more nucleic acids.

16. The method of claim 8, wherein the isolated DNA is associated with one or more protein.

* * * * *

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: synthetic BcgI restriction enzyme recognition
      sequence
<220> FEATURE:
<221> NAME/KEY: modified_base
<222> LOCATION: (4)...(9)
<223> OTHER INFORMATION: n = g, a, c or t

<400> SEQUENCE: 1
cgannnnnnt gc                                                        12
```